(12) United States Patent
Wax et al.

(10) Patent No.: US 6,814,966 B1
(45) Date of Patent: *Nov. 9, 2004

(54) METHODS FOR TREATING GLAUCOMA

(75) Inventors: Martin B. Wax, Wildwood, MO (US); Gulgun Tezel, Louisville, KY (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/591,561

(22) Filed: Jun. 13, 2000

Related U.S. Application Data

(63) Continuation-in-part of application No. 09/500,023, filed on Feb. 8, 2000, now Pat. No. 6,531,128.

(51) Int. Cl.[7] ............................................. A61K 39/395
(52) U.S. Cl. ................. 424/134.1; 424/427; 424/130.1; 424/145.1; 514/12; 514/2; 530/351
(58) Field of Search ........................... 424/130.1, 133.1, 424/134.1, 139.1, 141.1, 145; 514/12, 2

(56) References Cited

U.S. PATENT DOCUMENTS

| | | |
|---|---|---|
| 5,770,624 A | 6/1998 | Parker |
| 5,932,610 A | 8/1999 | Shohami et al. |
| 6,015,557 A | 1/2000 | Tobinick et al. |
| 6,177,077 B1 * | 1/2001 | Tobinick .................. 424/134.1 |
| 6,204,270 B1 * | 3/2001 | Ron et al. .................... 514/263 |

OTHER PUBLICATIONS

Yan X, et al., "Matrix Metalloproteinases and Tumor Necrosis Factor–alpha in Glaucomatous Optic Nerve Head", Archives Ophthalmol 2000; 118:666–673.

Tezel G, et al, Increased Production by Tumor Necrosis Factor–Alpha By Glial Cells Exposed To Simulated Ischemia Or Elevated Hydrostatic Pressure Induces Apoptosis in Co–Cultured Retinal Ganglion Cells:, The Journal of Neuroscience 2000; 20:8693–8700.

* cited by examiner

*Primary Examiner*—Yvonne Eyler
*Assistant Examiner*—Eileen B. O'Hara
(74) *Attorney, Agent, or Firm*—Eitan, Pearl, Latzer & Cohen Zedek, LLP; Mark S. Cohen

(57) ABSTRACT

This invention provides a method for treating a subject with glaucoma comprising the steps of administrating a compound or composition which antagonize, inhibits, inactivates, reduce, suppresses, antagonizes, and/or limits the release, synthesis, or production from cells of TNF-α thereby treating the subject with glaucoma.

8 Claims, 15 Drawing Sheets

US 6,814,966 B1

METHODS FOR TREATING GLAUCOMA

CROSS REFERENCE

This Application claims the benefit of and is a Continuation-in-Part Application of U.S. Ser. No. 09/500,023, filed Feb. 8, 2000, now U.S. Pat No. 6,531,128.

FIELD OF THE INVENTION

This invention provides a method for treating a subject with glaucoma comprising the steps of administrating a compound or composition which antagonize, inhibits, inactivates, reduce, suppresses, antagonizes, and/or limits the release, synthesis, or production from cells of TNF-α thereby treating the subject with glaucoma.

BACKGROUND OF THE INVENTION

The cytokine known as tumor necrosis factor (TNF or TNF-α) is structurally related to lymphotoxin. They have about 40 percent amino acid sequence homology (Old, Nature 330:602–603, 1987). These cytokines are released by macrophages, monocytes and natural killer cells and play a role in inflammatory and immunological events. The two cytokines cause a broad spectrum of effects both in vitro and in vivo, including: (i) vascular thrombosis and tumor necrosis; (ii) inflammation; (iii) activation of macrophages and neutrophils; (iv) leukocytosis; (v) apoptosis; and (vi) shock. TNF has been associated with a variety of disease states including various forms of cancer, arthritis, psoriasis, endotoxic shock, sepsis, autoimmune diseases, infections, obesity, and cachexia. TNF appears to play a role in the three factors contributing to body weight control; intake, expenditure, and storage of energy (Rothwell, Int. J. Obesity 17:S98–S101, 1993).

Histopathologic studies of the glaucomatous optic nerve head in primary open angle glaucoma (POAG) reveal astroglial activation and tissue remodeling, which accompanies neuronal damage. As a part of tissue remodeling, backward bowing and disorganization of the laminar cribriform plates are common characteristics of glaucomatous eyes with either normal or high intraocular pressure.[1] These histologic changes are accompanied by the upregulation of extracellular matrix components including collagen and proteoglycan, and adhesion molecules by optic nerve head astrocytes in glaucomatous eyes.[2-6] The astroglial activation seen in glaucomatous optic nerve heads likely represents an attempt to limit the extent of the injury and promote the tissue repair process. However, despite the astroglial activation, there is limited deposition of extracellular matrix in glaucomatous optic nerve atrophy, which does not retain characteristics of scar tissue formation.[7,8] This suggests that there are diverse cellular responses to the initial event or subsequent tissue injury, which preferentially results in tissue degradation.

In addition, reactive astrocytes following neuronal injury produce various neurotrophic factors and cytokines including TNF-α.[14] which play a critical role in the regulation of the synthesis of MMPs.[15-17] Furthermore, the release of TNF-α from its membrane-bound precursor is a MMPs-dependent process.[18] Matrix metalloproteinases (MMPs) are proteolytic enzymes that degrade components of extracellular matrix. Increased secretion of MMPs by activated glial cells have been implicated in various extracellular matrix remodeling events that occur during normal development and in a number of pathologies including atherosclerosis, arthritis, tumor growth, metastasis and glaucoma.[9-13]

TNF-α is a potent immuno-mediator and pro-inflammatory cytokine that is rapidly upregulated in the brain after injury. It is also known as an inducer of apoptotic cell death via TNF-α receptor-1 occupancy (Hsu H, Xiong J, Goeddel D V. The TNF receptor 1-associated protein TRADD signals cell death and NF-kappa B activation. *Cell*, 1995;81:495–504.).

Open angle glaucoma (OAG) the second leading cause of irreversible blindness in the United States, comprises 2 major syndromes: primary open angle glaucoma (POAG) and normal pressure glaucoma (NPG). POAG is a disease generally characterized by a clinical triad which consists of 1) elevated intraocular pressure (IOP); 2) the appearance of optic atrophy presumably resulting from elevated IOP; and 3) a progressive loss of peripheral visual sensitivity in the early stages of the disease, which may ultimately progress and impair central visual acuity. (Quigley, H A: Open angle glaucoma, New Engl J Med 1993; 328:1097–1106.) Studies have indicated, however, that a surprisingly high percentage of patients with OAG have findings identical to those in POAG but with a singular exception; namely, that the IOP has never been demonstrated to be elevated. Several large population-based studies have documented the high prevalence of this form of glaucoma, often called "low tension glaucoma" (but more accurately called "normal pressure glaucoma") (NPG). The most conservative of these estimates place the percentage of glaucoma that occurs in the presence of "normal" IOP at approximately 20–30% (Sommer A, Intraocular pressure and glaucoma. *Am J Ophthalmol* 1989;107:186–188, and Sommer A. Doyne Lecture, Glaucoma: Facts and Fancies. *Eye* 1996;10:295–301.)

In addition to the most common forms of glaucoma described above, there are secondary and closed angle forms of glaucoma which typically result in elevated intraocular pressure due to a variety of mechanisms. In virtually all these other forms of glaucoma, elevated eye pressure is found, and a characteristic optic neuropathy similar to that found in OAG ensues. If untreated, elevated intraocular pressure in these glaucomas invariably leads to visual loss and eventual blindness. In many forms of glaucoma, including those with normal intraocular pressure, lowering of intraocular pressure often fails to halt the progression of the disease. Comparison of glaucomatous progression between untreated patients with normal-tension glaucoma and patients with therapeutically reduced intraocular pressures. Collaborative Normal-Tension Glaucoma Study Group. Am J Ophthalmol. 1998 October;126(4):487–97.)

During development and maintenance of the nervous system there exists a complex interdependency between neurons and glial cells. The glial cells maintain normal functioning of the nervous system both by controlling the extracellular environment and by supplying metabolites and growth factors. After damage to the central nervous system, glial cells are thought to support neural growth and metabolism and to scavenge agents toxic to neurons. However, recent evidence challenges the view that glial cells are purely neuroprotective and rather suggests that they could participate in damaging neurons. For example, following focal cerebral ischemia or during the course of neurodegenerative diseases or trauma, reactive astrocytes as well as microglia within the central nervous system produce cytokines, reactive oxygen species and nitric oxide (NO), which are implicated as mediators of tissue injury.

SUMMARY OF THE INVENTION

As provided herein, the invention provides a compound or composition containing an agent or molecule which antagonize, inhibits, inactivates, reduce, suppresses, antagonizes, and/or limits the release, synthesis, or production from cells of TNF-α. Such a composition is beneficial for the treatment of glaucoma.

This invention provides a method for treating a subject with glaucoma comprising the steps of administrating a compound agent or composition containing an agent, compound, or molecule, including analogs, isomers, homologues, fragments or variants thereof, which antagonize, inhibits, inactivates, reduce, suppresses, antagonizes, and/or limits the release, synthesis, or production from cells of TNF-α thereby treating the subject with glaucoma.

In one embodiment, the agent, compound, or molecule suppresses the level or production of TNF-α. In another embodiment, the agent, compound, or molecule inhibits the production of TNF-α.

In another embodiment, the agent, compound, or molecule limits the synthesis or release of TNF-α from cells. In another embodiment, the compound is thalidomide. In another embodiment, the compound is a selective cytokine inhibitor. In another embodiment, the inhibitor is rolipram or phosphodiesterase 4 inhibitor.

In another embodiment, the agent, compound, or molecule inactivates circulating TNF-α In another embodiment, the molecule is anti-TNF-α antibody. In another embodiment, the molecule is infliximab. In another embodiment, the molecule is recombinant TNF-α soluble receptors. In another embodiment, the molecule is etanercept.

This invention provides a TNF reducer which is hydrazine sulfate, pentoxifylline, ketotifen, tenidap, vesnarinone, cyclosporine, peptide T, sulfasalazine, thorazine, antioxidants, corticosteroids, marijuana, glycyrrhizin, sho-saiko-to, L-carnitine, hyperthermia, or hyperbaric oxygen therapy.

Lastly, this invention provides a method of assaying a subjects serum level of TNF alpha as an indicator for treatment with TNF inhibitors. The assay measures the level of several cytokines in the serum of the subject such as interleukion 10 and interferon gamma.

DETAILED DESCRIPTION OF THE INVENTION

Figure 1:
FIG. 1. Immunoperoxidase staining for TNF-α in the human optic nerve head. There was faint immunostaining of a few glial cells around the nerve bundles and blood vessels (v) in the prelaminar region of the control optic nerve head. (A). However, the intensity of the immunostaining and the number of stained glial cells were greater in the optic nerve heads from patients with primary open angle glaucoma (B) or normal pressure glaucoma (C) (gc, glial column; nb, nerve bundles; cs, cavernous spaces) (Chromagen, DAB; Nuclear counterstain with Mayer's hematoxylin; original magnification×100).

Although glial cells in the optic nerve head undergo an activation process in glaucoma, the role of glial cells during glaucomatous neurodegeneration of retinal ganglion cells is unknown. Using a co-culture system, the influences of glial cells on survival of retinal ganglion cells following exposure to different stress conditions typified by simulated ischemia and elevated hydrostatic pressure was studied. Following exposure to these stressors, it was observed that glial cells secreted TNF-α as well as other noxious agents such as nitric oxide into the co-culture media and facilitated apoptotic death of retinal ganglion cells as assessed by morphology, TUNEL and caspase activity. The glial origin of these noxious effects was confirmed by passive transfer experiments. Furthermore, retinal ganglion cell apoptosis was attenuated approximately 66% by a neutralizing antibody against TNF-α and 50% by a selective inhibitor (1400W) of inducible nitric oxide synthase. Since elevated intraocular pressure and ischemia are two prominent stress factors identified in the eyes of patients with glaucoma, these findings reveal a novel pathogenic mechanism for retinal ganglion cell death in glaucoma. In addition, these studies show that inhibition or neutralization of TNF-α released by activated glial cells may provide a novel therapeutic target for neuroprotection in the treatment of glaucomatous optic neuropathy. This invention provides evidence that elevated hydrostatic pressure as well as simulated ischemia can initiate the apoptotic cell death cascade in retinal ganglion cells largely due to the activity of glial cells in response to these stressors. Apoptosis-promoting substances, including TNF-α secreted by activated glial cells after exposure to stress, contribute directly to neuronal cytotoxicity. Further, as shown herein, increased expression of TNF-α and its receptor in the glaucomatous optic nerve head and retina demonstrate a role of this cytokine in the neurodegenerative process of glaucoma, which provides a novel therapeutic target for the management of glaucoma.

This invention provides a method for treating a subject with glaucoma comprising the steps of administrating an agent, compound, or molecule or a composition containing an agent, compound, or molecule, including analogs, isomers, homologues, fragments or variants thereof, which antagonize, inhibits, inactivates, reduce, suppresses, antagonizes, and/or limits the release, synthesis, or production from cells of TNF-α thereby treating the subject with glaucoma In one embodiment, the agent, compound, or molecule suppresses the level or production of TNF-α. In another embodiment, the agent, compound, or molecule inhibits the production of TNF-α.

In another embodiment, the agent, compound, or molecule limits the synthesis or release of TNF-α from cells. In another embodiment, the compound is thalidomide. In another embodiment, the compound is a selective cytokine inhibitor. In another embodiment, the inhibitor is rolipram or phosphodiesterase 4 inhibitor.

In another embodiment, the agent, compound, or molecule inactivates circulating TNF-α. In another embodiment, the molecule is anti-TNF-α antibody. In another embodiment, the molecule is infliximab. In another embodiment, the molecule is recombinant TNF-α soluble receptors. In another embodiment, the molecule is etanercept.

In another embodiment, the compound or composition containing a molecule which inactivated circulating TNF. In another embodiment, the molecule is anti-TNF antibody. In another embodiment, the molecule is infliximab. In another embodiment, the molecule is recombiaant TNF soluble receptors. In another embodiment, the molecule is etanercept. In one embodiment, a selective inhibitor of inducible nitric oxide synthase is provided in combination with the molecules which inactivated circulating TNF or TNF-α reducer.

This invention provides a TNF-α reducer which in one embodiment is hydrazine sulfate, pentoxifylline, ketotifen, tenidap, vesnarinone, cyclosporine, peptide T, sulfasalazine, thorazine, antioxidants, corticosteroids, marijuana, glycyrrhizin, sho-saiko-to, L-carnitine, hyperthermia, or hyperbaric oxygen therapy.

The experiments herein, provide evidence that the functional state of glial cells determined by environmental factors may be important for determining the ultimate role of glial cells as either neuroprotective or neurotoxic. The retinal glial cells exposed to stress conditions such as elevated hydrostatic pressure or simulated ischemia have neurotoxic influence on retinal ganglion cells. Alterations in the functional state of glial cells in response to stress conditions similar to that created during the process of glaucoma lead to retinal ganglion cell death due to increased production of death-promoting substances, including TNF-α. These findings reveal a novel pathogenic mechanism for retinal ganglion cell death in glaucoma and provide a novel therapeutic target for neuroprotection in the treatment of glaucomatous optic neuropathy.

In the current study, cell survival was examined in primary co-cultures of retinal ganglion cells and glial cells exposed to elevated hydrostatic pressure for a longer period (up to 72 hours) and it was demonstrated that the elevated hydrostatic pressure decreased neuronal survival. Increased production of apoptosis promoting substances by retinal glial cells following exposure to elevated hydrostatic pressure or simulated ischemia, accounts, in part, for the increased rate of cell death in co-cultured retinal ganglion cells. Passive transfer experiments confirmed that the source of noxious insults on retinal ganglion cells was retinal glial cells exposed to stress conditions.

In addition to TNF-α, as shown herein increased production of NO in retinal glial cells exposed to different stress conditions induced cell death in co-cultured retinal ganglion cells. The experiments herein using inhibitors of TNF-α or iNOS revealed an inhibition of apoptotic cell death in retinal ganglion cells in co-cultures exposed to simulated ischemia or elevated hydrostatic pressure. While iNOS inhibition provided partial protection against apoptotic cell death in co-cultures, more prominent inhibition of apoptosis was observed following inhibition of TNF-α. These results demonstrate a crucial role for endogenous TNF-α in mediating neurotoxicity in cultured retinal ganglion cells. Since TNF-α induces NO secretion, inhibition of its activity thus indirectly decrease the harmful effect created by NO as well. Similar to the observations herein, neutralizing anti-TNF-α antiserum, rather than a NOS inhibitor, inhibited neurotoxicity of cytokine-induced production of iNOS and TNF-α in neuron-astrocyte cultures derived from human fetal cerebrum.

Neutralization of systemic TNF-α ameliorates target organ damage in these diseases. Two drugs which effectively neutralize the adverse effects of TNF-α in rheumatoid diseases are Remicade (Centocor, Malvern, Pa.), a chimeric monoclonal antibody to TNF-α (Knight D M, Trinh H, Le J, Siegel S, Shealy D, McDonough M, Scallon B, Moore M A, Vilcek J, Daddona P, Ghrayeb J. Construction and initial characterization of a mouse-human chimeric anti-TNF antibody. *Mol Immunol.* 1993;30:1443–1453; Elliot M J, Maini R N, Feldmann M, Kalden J R, Antoni C, Smolen J S, Leeb B, Breedveld F C, Macfarlane J D, Bijl H, Woody J N. Randomised double-blind comparison of chimeric monoclonal antibody to tumour necrosis factor α (cA2) versus placebo in rheumatoid arthritis. *Lancet.* 1994;344:1105–1110; Targan S R, Hanauer S B, van Deventer S J, Mayer L, Present D H, Braakman T, DeWoody K L, Schaible T F, Rutgeerts P J. A short-term study of chimeric monoclonal antibody cA2 to tumor necrosis factor alpha for Crohn's disease. Crohn's Disease cA2 Study Group. *N Engl J Med.* 1997;337:1029–1035.) and Enbrel (Immunex, Seattle, Wash.), a biologically engineered copy of TNFα receptor p75-Fc Fusion protein (Weinblatt M E, Kremer J M, Bankburst A D, Bulpitt K J, Fleischmann R M, Fox R I, Jackson C G, Lange M, Burge D J. A trial of etanercept, a recombinant tumor necrosis factor receptor:Fc fusion protein, in patients with rheumatoid arthritis receiving methotrexate. *N Engl J Med.* 1999;340:253–259.).

This indicates a significant role of TNF-α in the neurodegenerative process seen in glaucoma, drugs inhibiting its function are an attractive targets to decrease cell death in glaucoma. In addition, since TNF-α is a stimulator of nitric oxide synthesis (Romero L I, Tatro J B, Field J A, Reichlin S. Roles of IL-1 and TNF-alpha in endotoxin-induced activation of nitric oxide synthase in cultured rat brain cells. *Am J Physiol.* 1996;270:R326–332; Goureau O, Amiot F, Dautry F, Courtois Y. Control of nitric oxide production by endogenous TNF-alpha in mouse retinal pigmented epithelial and Muller glial cells. *Biochem Biophys Res Commun.* 1997;240:132–135, Heneka M T, Loschmann P A, Gleichmann M, Weller M, Schulz J B, Wullner U, Klockgether T. Induction of nitric oxide synthase and nitric oxide-mediated apoptosis in neuronal PC12 cells after stimulation with tumor necrosis factor-alpha/lipopolysaccharide. *J Neurochem.* 1998;71:88–94.), treatment with TNF-α antagonists, inhibitors, inactivators, reducers, suppressors, or agents which antagonize, and/or limits the release, synthesis, or production from cells of TNF-α reduce nitric oxide synthase-2 expression and activity (Perkins D J, St Clair E W, Misukonis M A, Weinberg J B. Reduction of NOS2 overexpression in rheumatoid arthritis patients treated with anti-tumor necrosis factor monoclonal antibody (cA2). *Arth Rheum.* 1998;41:2205–2210.). Therefore, blockade, amelioration or attentuation of TNF-α is also effective on inhibiting, reducing or preventing nitric oxide synthase-related cell death which is known as an important mediator of neuronal cell death, and may be a causal factor in glaucoma (Neufeld A H, Sawada A, Becker B. Inhibition of nitric-oxide synthase 2 by aminoguanidine provides neuroprotection of retinal ganglion cells in a rat model of chronic glaucoma Proc Natl Acad Sci USA 1999 Aug. 17;1996(17): 9944–8)

The type of glaucoma for which the invention is applicable includes but is not limited to: primary open angle glaucoma, normal pressure glaucoma, pigmentary glaucoma, pseudoexfoliation glaucoma, acute angle closesure glaucoma, absolute glaucoma chronic glaucoma, congenital glaucoma, juvenile glaucoma, narrow angle glaucoma, chronic open angle glaucoma and simplex glaucoma.

As provided herein, the Tumor Necrosis Factor (TNF) superfamily of cytokines includes both soluble and membrane-bound proteins that regulate cellular activation (including immune responses and inflammatory reactions), cellular viability and proliferation, NF-kappa B activation, and also the pathology of various diseases. TNF-α is a cytokine produced by macrophages and lymphocytes which mediates inflammatory and immunopathological responses. TNF-α has been implicated in the progression of diseases which include but are not limited to immunomodulation disorder, infection, cell proliferation, angiogenesis (neovascularisation), tumour metastasis, apoptosis, sepsis, and endotoxaemia. The necrotising action of TNF in vivo mainly relates to capillary injury. TNF causes necrosis not only in tumour tissue but also in granulation tissue. It causes morphological changes in growth inhibition of and cytoxicity against cultured vascular endothelial cells (Haranka et al 1987 Ciba Found Symp 131: 140–153).

Expression of TNF receptors on both lymphoid and non-lymphoid cells can be influenced experimentally by many different agents, such as bacterial lipopolysaccharide (LIPS), phorbol myristate acetate (PMA; a protein kinase C activator), interleukin-1 (IL-1), interferon-gamma (IFN-y) and IL-2 (Gatanaga et al. Cell Immuno/. 138:1–10, 1991; Yui et al. Placenta 15:819–935, 1994). It has been shown that complexes of human TNF bound to its receptor are internalized from the cell membrane, and then the receptor is either degraded or recycled (Armitage, Curr. Opin. Immunol. 6:407–413, 1994). TNF receptor activity can be modulated using peptides that bind intracellularly to the receptor, or which bind to the ligand binding site, or that affect receptor shedding. See for example patent publications WO 95/31544, WO 95/33051, WO 96/01642, and EP 568 925.

TNF binding proteins (TNF-BP) have been identified at elevated levels in the serum and urine of febrile patients, patients with renal failure, and cancer patients, and even certain healthy individuals. Human brain and ovarian tumors produced high serum levels of TNF-BP These molecules have been purified, characterized, and cloned (Gatanaga et al., Lymphokine Res. 9:225–229, 1990a; Gatanaga et al., Proc. Nat/. Acad. Sci USA 87:8781–8784, 1990b). Human TNF-BP consists of 30 kDa and 40 kDa proteins which are identical to the N-terminal extracellular domains of p55 and p75 TNF receptors, respectively (U.S. Pat. No. 5,395,760; EP 418,014). Such proteins have been suggested fox use in treating endotoxic shock. Mohler et al. J. Immunol. 151:1543–1561, 1993 There are several mechanisms possible for the production of secreted proteins resembling membrane bound receptors. One, involves translation from alternatively spliced mRNAs lacking transmembrane and cytoplasmic regions.

A "TNF modulator" is a compound that has the property of either increasing or decreasing TNF activity for processing TNF on the surface of cells.

Etanercept (Brand name Embrel) is known to those skilled in the art. Etanercept is a recombinant form of the human tumor necrosis factor receptor fused to the Fc fragment of a human IgG1 molecule. The resulting form is a dimeric molecule that can bind two circulating tumor necrosis factor (TNF) molecules. This binding prevents TNF from interacting with the cell surface TNF receptors, inhibiting its role in the joint pathology. Currently there are two TNF receptors that have been identified (p75 and p55) and both have the same affinity for TNF. Etanercept is supplied in a carton containing four dose trays; each tray contains one 25 mg single-use vial of etanercept, one syringe (1 mL Sterile Bacteriostatic Water for Injection, USP containing 0.9% benzyl alcohol), one plunger, and 2 alcohol swabs. The recommended dose of etanercept for adult patients is 25 mg given twice weekly as a subcutaneous injection.

Infliximab (Remicade) is known to those skilled in the art. Infliximab (Remicade) is a chimeric $IgG1_k$ monoclonal antibody produced by a recombinant cell line to treat Crohn's disease. Infliximab (Remicade) acts by neutralizing the biological activity of TNFb by high-affinity binding to its soluble and transmembrane forms and inhibits TNFb receptor binding.

Homologue means a polypeptides having the same or conserved residues at a corresponding position in their primary, secondary or tertiary structure. The term also extends to two or more nucleotide sequences encoding the homologous polypeptides.

A "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g, restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i e., the strand having a sequence homologous to the mRNA). A "recombinant DNA" is a DNA that has undergone a molecular biological manipulation.

"Substantial identity" or "substantial sequence identity" mean that two sequences, when optimally aligned, such as by the programs GAP or BESTFIT using default gap which share at least 65–99 percent sequence identity, share at least 75 percent sequence identity, share at least 80 percent sequence identity, share at least 90 percent sequence identity, preferably at least 95 percent sequence identity, more preferably at least 99 percent sequence identity or more. The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

A "fusion polypeptide" is a polypeptide comprising regions in a different position in the sequence than occurs in nature. The regions can normally exist in separate proteins and are brought together in the fusion polypeptide; they can normally exist in the same protein but are placed in a new arrangement in the fusion polypeptide; or they can be synthetically arranged. A "functionally equivalent fragment" of a polypeptide varies from the native sequence by addition, deletion, or substitution of amino acid residues, or any combination thereof, while preserving a functional property of the fragment relevant to the context in which it is being used. Fusion peptides and functionally equivalent fragments are included in the definition of polypeptides used in this disclosure.

It is understood that the folding and the biological function of proteins can accommodate insertions, deletions, and substitutions in the amino acid sequence. Some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are described in Altschul et al. Bull. Math. Bio. 48:603–616, 1986; and Henikoff et al. Proc. Natl. Acad. Sci. USA 89:10915–10919, 1992.

Substitutions that preserve the functionality of the polypeptide, or confer a new and beneficial property (such as enhanced activity, stability, or decreased immunogenicity) are especially preferred.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also antibody equivalents that include at least one antigen combining site of the desired specificity. These include but are not limited to enzymatic or recombinantly produced fragments antibody, fusion proteins, humanized antibodies, single chain variable regions, diabodies, and antibody chains that undergo antigen-induced assembly. In one embodiment the antibody is a monoclonal antibody. In another embodiment the antibody is a polyclonal antibody. The antibody may be chimeric, human or murine or a hybrid thereof which are known to those skilled in the art. Specifically binds to an "antibody" or "specifically immunoreactive with", when referring to the recombinant antibody or proteins refers to the binding of a cell or protein to the TNF so as to modulate, decrease, suppress, inactivate the activity of TNF.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

Antibodies Polyclonal antibodies can be prepared by injecting a vertebrate with a polypeptide of this invention in an immunogenic form. Immunogenicity of a polypeptide can be enhanced by linking to a carrier such as KLH, or combining with an adjuvant, such as Freund's adjuvant. Typically, a priming injection is followed by a booster injection is after about 4 weeks, and antiserum is harvested a week later. Unwanted activity cross-reacting with other antigens, if present, can be removed, for example, by running the preparation over adsorbants made of those antigens attached to a solid phase, and collecting the unbound fraction. If desired, the specific antibody activity can be further purified by a combination of techniques, which may include protein, A chromoatography, ammonium sulfate precipitation, ion exchange chromatography, HPLC, and immunoaffinity chromatography using the immunizing polypeptide coupled to a solid support. Antibody fragments and other derivatives can be prepared by standard immunochemical methods, such as subjecting the antibody to cleavage with enzymes such as papain or pepsin.

The antibody may be labeled with a detectable marker including, but not limited to: a radioactive label, or a colorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include but are not limited to: fluorescein, rhodamine and auramine. Colorimetric markers include, but are not limited to: biotin, and digoxigenin. Examples of types of labels encompassed by the present invention include, but are not limited to, radioisotopic labels (e.g., $^{3}H$, $^{125}I$, $^{131}I$, $^{35}S$, $^{14}C$, etc.), non-radioactive isotopic labels (e.g., $^{55}Mn$, $^{56}Fe$, etc.), fluorescent labels (e.g., a fluorescein label, an isothiocyanate label, a rhodamine label, a phycoerythrin label, a phycocyanin label, an allophycocyanin label, art O-phthaldehyde label, a fluorescamine label, etc.) for example, as in peridinin chlorophyll protein (PerCP), chemiluminescent labels, enzyme labels (e.g., alkaline phosphatase, horse radish peroxidase, etc.), protein labels, labels useful in radioimaging and radioimmunoimaging.

Variant(s), as the term is used herein, are polynucleotides or polypeptides that differ from a reference polynucleotide or polypeptide respectively. Variants in this sense are described below and elsewhere in the present disclosure in greater detail. (1) A polynucleotide that differs in nucleotide sequence from another, reference polynucleotide. Changes in the nucleotide sequence of the variant may be silent, i.e., they may not alter the amino acids encoded by the polynucleotide. Where alterations are limited to silent changes of this type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination. (3) A variant may also be a fragment of a polynucleotide or polypeptide of the invention that differs from a reference polynucleotide or polypeptide sequence by being shorter than the reference sequence, such as by a terminal or internal deletion. A variant of a polypeptide of the invention also includes a polypeptide which retains essentially the same biological function or activity as such polypeptide, e.g., proproteins which can be activated by cleavage of the proprotein portion to produce an active mature polypeptide. (4) A variant may also be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is, employed for purification of the mature polypeptide or a proprotein sequence. (5) A variant of the polynucleotide or polypeptide may be a naturally occurring variant such as a naturally occurring allelic, variant, or it may be a variant that is not known to occur naturally. Such non-naturally occurring variants of the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or noncoding regions or both. Alterations in the coding regions may produce conservative or non-conservative amino acid substitutions, deletions or additions. All such variants defined above are deemed to be within the scope of those skilled in the art from the teachings herein and from the art.

Antisense nucleotides or polynucleotide sequences are useful in preventing or diminishing the expression of TNF are known to those skilled in the art. Also, this invention provides an antisense molecule capable of specifically hybridizing with TNFα to inhibit or repress production of TNFα. This invention provides an antagonist capable of blocking the expression of TNF. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of TNF.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein.

Oligonucleotides which are complementary to TNF and which may bind to TNF and inhibit production of TNF may be obtained as follows: The polymerase chain reaction is then carried out using the two primers. See PCR Protocols:
A Guide to Methods and Applications [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein. High stringent hybridization conditions are selected at about 5 C lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60 C. As other factors may significantly affect the stringency of hybridization, including, among others, base composition and size of the complementary strands the presence of organic solvents, ie. salt or formamide concentration, and the extent of base mismatching, the combination of parameters is more important than the absolute measure of any one. For Example high stringency may be attained for example by overnight hybridization at about 68 C in a 6×SSC solution, washing at room temperature with 6×SSC solution, followed by washing at about 68 C in a 6×SSC in a 0.6×SSX solution.

Hybridization with moderate stringency may be attained for example by: 1) filter pre-hybridizing and hybridizing with a solution of 3×sodium chloride, sodium citrate (SSC), 50% formamide, 0.1M Tris buffer at Ph 7.5, 5×Denhardt's solution; 2.) pre-hybridization at 37 C for 4 hours; 3) hybridization at 37 C with amount of labelled probe equal to 3,000,000 cpm total for 16 hours; 4) wash in 2×SSC and 0.1% SDS solution; 5) wash 4× for 1 minute each at room temperature at 4× at 60 C for 30 minutes each; and 6) dry and expose to film.

The phrase "selectively hybridizing to" refers to a nucleic acid probe that hybridizes, duplexes or binds only to a particular target DNA or RNA sequence when the target sequences are present us a preparation of total cellular DNA or RNA. By selectively hybridizing it is meant that a probe binds to a given target in a manner that is detectable in a different manner from nontarget sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

As used herein, "phamaceutical composition" means therapeutically effective amounts of the compound or composition containing the molecule of the invention as described above together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, intratumorally, paracancerally, transmucosally, transdermally, intramuscularly, intravenously, intradermally, intravascularly, subcutaneously, intraperitonealy, intraventricularly, intracranially, topical drops or ointment, periocular injection, systemically by intravenous injection or orally, intracamerally into the anterior chamber or vitreous, via a depot attached to the intraocular lens implant inserted during surgery, or via a depot placed in the eye sutured in the anterior chamber or vitreous.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobial, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif. p. 384.). Often, a primary challenge with an antigen alone, in the absence of an adjuvant, will fail to elicit a humoral or cellular immune response. Adjuvant include, but are not limited to, complete Freud's adjuvant, incomplete Freud's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutically acceptable form of the composition includes a pharmaceutically acceptable carrier. In the therapeutic methods and compositions of the invention, a therapeutically effective dosage of the active component is provided. A worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous, infusion sufficient to maintain concentrations of ten nanomolar to ten micromolar in the blood are contemplated.

The following examples are presented in order to more fully illustrate the preferred embodiments of the invention. They should in no way be construed, however, as limiting the broad scope of the invention.

EXPERIMENTAL DETAILS SECTION

EXAMPLE 1

Materials and Methods

Patients. Four postmortem human eyes with a diagnosis of POAG and seven human eyes with a diagnosis of NPG were obtained. The age of patients ranged from 68 to 84 years. The clinical findings of the glaucoma patients were well documented during 5–13 years (mean 7.5 years) of follow-up during which intraocular pressure readings, optic disc assessments and visual field tests were obtained. Four human donor eyes with no history of eye disease were used as age-matched controls (age range 61 to 81 years). The death to fixation time for the specimens ranged between 6–9 hours. After enucleation, all eyes were fixed in 10% neutral buffered formalin for 24 hours, dehydrated in graded alcohol and embedded in paraffin. Since some of the specimens only contained the optic nerve head and small portions of the peripapillary retina, retinal distribution of immunostaining was not studied. Following deparaffinization, 5 μm-thickness longitudinal sections of optic nerve heads were incubated with monoclonal antibodies against MMP-1, MMP-2 or MMP-3 (2.5 μg/ml) (Oncogene Science, Cambridge, Mass.) or polyclonal antibodies against TNF-α or TNF-α receptor-1 (2 μg/ml) (R&D Systems, Minneapolis, Minn.) overnight at 4° C., after endogenous peroxidase was blocked with 2% hydrogen peroxide in methanol and followed by several washes in phosphate buffered saline solution. The three anti-MMP antibodies recognized both latent as well as active forms of MMPs. Prior to incubation with primary antibodies, the sections were incubated with either mouse skin extract (during MMP staining) or 20% non-immune donkey serum (during TNF and its receptor staining) for 20 minutes to block background staining. Biotinylated secondary antibody (anti-mouse or anti-goat IgG) (Daco Corporation, Carpinteria, Calif.) was applied to the sections for 30 minutes at room temperature. The slides were then incubated with horseradish peroxidase-labeled streptavidin solution (Dako Corporation) for 30 minutes, and the reaction was visualized by incubation in a solution of 0.02% 3-3' diaminobenzidine tetrahydrochloride (DAB) and 0.006% $H_2O_2$ in 0.05 M Tris-Hcl (pH. 7.6). The slides were lightly counterstained with Mayer's hematoxylin. Sections incubated with mouse serum or phosphate buffered saline solution in place of the primary antibody served as negative controls. Sections from biopsy specimens of infiltrating ductal breast carcinoma served as a positive control for all antibodies used in this study.

Three to 5 sections from each optic nerve head were examined by immunohistochemistry for each protein including MMPs, TNF-α and its receptor. In order to obtain comprehensive semiquantitative evaluation of the immunostaining, the intensity of immunostaining for MMPs, TNF-α and its receptor in the prelaminar, laminar and postlaminar regions of the optic nerve head was graded using an arbitrary score in which each region was graded from – to +++. A semiquantitative score (indicated in parentheses) was then calculated for each optic nerve head [–=absent (0), ±=range from absent to weak (0.5), +=weak staining (1), ++=moderate staining (2), ++=strong staining (3)]. The grading of the immunostaining was performed in a masked fashion by an observer who was skilled in grading immunohistochemical staining but was not familiar with the pathologic changes in the optic nerve head. The observer graded the intensity of immunostaining in optic nerve head regions (prelaminar, laminar, postlaminar) that were pointed out by one of the authors (XY). Both the scored results and the photographs of representative sections from each group are presented.

RESULTS

By light microscopy, the normal eyes exhibited glial columns and nerve bundles in the prelaminar region. In the lamina cribrosa, there were glial cells lining the collagenous laminar beams. In the postlaminar region the glial cells were mainly distributed along the pial septae and were also scattered among the axonal bundles.

The glaucomatous eyes either with POAG or NPG demonstrated axonal atrophy and backward bowing of the lamina cribrosa. The degree of the laminar bowing was comparable in the eyes with POAG or NPG. The degree of axonal atrophy was mild to moderate in the eyes with POAG and was especially noted in the postlaminar region. In the eyes with NPG the axonal atrophy was moderate in most eyes and characterized with focal loss in the areas of cavernous degeneration. In one eye with NPG, severe axonal loss was noted through the optic disc cup with axonal preservation in more peripheral areas. The postlaminar region of the optic nerve head in the eves with POAG demonstrated mild disorganization of the pial septae without tissue destruction. These changes were uniformly consistent in all eyes with POAG. In contrast, the eyes from the patients with NPG exhibited varying stages of Schnabels cavernous degeneration that was evident mainly at the lamina cribrosa and the postlaminar optic nerve. Axonal atrophy accompanied multifocal destruction of the cribriform laminar plates or pial septae within the cavernous degeneration areas seen in the eyes with NPG. In some eyes the areas of degeneration coalesced to form large cavernous spaces. In the areas of preserved axons the arrangement of laminar plates and pial septae remained intact and the distribution of glial cells remained unchanged.

Examinations of the optic nerve heads using immunohistochemistry revealed that the intensity of the immunostaining and the number of stained cells for MMPs, TNF or TNF-α receptor-1 were greater in the glaucomatous optic nerve heads, particularly with NPG, compared to age-matched controls. The immunolabeling appeared to be mainly in cells that resembled astrocytes by morphology. Since this table reflects the changes in the intensity of immunostaining but not the number of stained cells, photographs are also presented to optimally reflect changes that occur in glaucomatous optic nerve heads. Immunostaining patterns of optic nerve heads for TNF-α and TNF-α receptor-1 is also given below. TNF-α. In control eyes there was faint immunostaining for TNF-α and its receptor, TNF-α receptor-1, in the processes of a few glial cells and around the nerve bundles and blood vessels of the optic nerve head. In glaucomatous optic nerve heads, the intensity of immunostaining and the number of stained cells for TNF-α or TNF-α receptor-1 were increased in all regions of the glaucomatous optic nerve head compared to controls. Immunostaining was positive in glial cells around the axons and vessels in the prelaminar and laminar regions of the optic nerve head in the glaucomatous eyes. In the postlaminar region the glial cells distributed along the pial septae and scattered among the nerve bundles exhibited immunostaining. Although immunostaining for TNF-α was mostly associated with glial cells, an increased immunostaining for TNF-α receptor-1 was also observed in the nerve bundles, which was prominent in the prelaminar region of the glaucomatous optic nerve heads.

DISCUSSION

The integrity and turnover of the extracellular matrix is influenced by many factors, which includes MMPs. Matrix metalloproteinases are a family of proteolytic enzymes secreted by glial cells and are capable of degrading almost all components of the extracellular matrix. The MMPs have been divided into 3 broad families based on their domain structure and substrate specificity. Interstitial collagenase (MMP-1) and neutrophil collagenase (MMP-8) belong to the collagenase family and their major substrates are fibrillar collagen type I, II and III. The enzymes MMP-2 and MMP-9 are members of the gelatinase family and their substrates include type IV and V collagen, fibronectin, proteoglycans and gelatin. Members of the stromelysin family include MMP-3 (stromelysin, transin) and MP-7 (matrilysin) and act on a wide range of substrates including protcoglycans, laminin, fibronectin, gelatin and procollagen precursor peptides.[15,19-23]

Although they are implicated in several diseases of the central nervous system,[11-13] little is known about the role of MMPs in either normal or glaucomatous human optic nerves. The localization of MMP-3 and MMP-2 and tissue inhibitor of metalloproteinases (TIMP-1) have been shown to be present in the normal primate optic nerve head and retina (Johnson et al, ARVO abstract, 1993). In addition, increased gelatinase activity has been found in glaucomatous monkey eyes (Emi et al, ARVO absract, 1993; Sawaguchi et al, ARVO absract, 1998). The observation of the mild MMP immunolabeling of the glial cells in normal optic nerve head and increased immunolabeling of MMPs in glaucomatous eyes is consistent with these limited studies.

The observations revealed that the intensity of immunostaining for MMPs. TNF-α and TNF-α receptor-1 was greater in glaucomatous optic nerve heads compared to controls. In addition, differential immunostaining patterns for these proteins were noted in the prelaminar, laminar and postlaminar regions of the optic nerve head. Some of these differential patterns included the most prominent labeling of MMPs in the postlaminar region and the most prominent labeling of TNF-α and its receptor in the prelaminar region of the glaucomatous optic nerve heads. One possible explanation of these findings may be based on the recently described regional and functional heterogeneity of glial cells in the optic nerve head. For example, the size and the density of type 1B astrocytes in the prelaminar and laminar regions, and the type 1A astrocytes in postlaminar region are greater in glaucomatous eyes than those in normal tissue.[24-26]

Increased immunostaining of MMPs was noted in the cytoplasm of astroglial cells and their processes as well as in the extracellular matrix of optic nerve head in the eyes with POAG or NPG. The distribution of increased immunostaining for MMPs in the different regions of optic nerve head was comparable in the eyes with POAG or NPG. However, the intensity of immunostaining for MMPs, especially for MMP-2, was greater in the eyes with NPG compared to the eyes with POAG. In the eyes with NPG, immunostaining along the pial septae was moderately increased in the region of cavernous degeneration.

Cells secrete MMP's in an inactive form and the proenzyme can be activated in the extracellular space by various molecules. The antibodies used to recognize MMP's in this study identify both MMP precursors and the proteolytically processed active forms. Therefore, immunohistochemistry cannot distinguish the functional state in which the MMPs are present within the tissue. The abundance of immunoreactivity in the astrocytes suggests the presence of a large pool of intracellular MMPs that might function at relatively low levels in the extracellular space under normal conditions. Such pools could possibly be rapidly activated to act on substrates in the extracellular matrix under pathologic conditions.[23]

The generalized increase in the expression of MMPs in the glaucomatous optic nerve head may have various consequences. Since MMPs are responsible for the degradation of the extracellular matrix components, their increased expression in the glaucomatous optic nerve head may represent a physiological response to counteract the increased extracellular matrix deposition that occurs in glaucomatous optic nerve head.[27] This may explain the absence of glial scar tissue in glaucomatous optic nerves despite astroglial activation. It is tempting to speculate that tissue degeneration resulting from increased MMP activity may, in part, account for the excavated appearance of optic disc cupping that accompanies glaucomatous optic neuropathy regardless of other factors such as intraocular pressure.

Matrix metalloproteinases have been proposed to play a role in axonal growth by preventing scar tissue formation, in vivo,[29,30] which is thought to be a barrier to trophic substances necessary for neuronal regeneration.[31] Therefore, the observation of prominent immunostaining for MMPs in the areas of preserved axons may signify that activated glial cells increase secretion of MMPs for the dual purposes of preventing scar tissue formation while simultaneously promoting neuronal growth.

The pial septae of the normal optic nerve contains collagen type III, IV and fibronectin mainly around the blood vessels.[31] These are the major substrates of MMP-2 and MMP-3. The increased immunostaining of MMP-2 and MMP-3 in the astrocytes and along the pial septae in the glaucomatous optic nerve head suggests that these MMP's may play a role in the disruption of pial septa seen in the areas of cavernous degeneration.

In addition, expression of MMP-2 increased in the astrocytic processes enveloping blood vessels in the glaucomatous optic nerve head, particularly in the eyes with NPG. Since MMP-2 causes a thinning of the basal lamina and an increase in the capillary permeability,[32] it seems possible that increased expression of MMPs in the perivascular area may influence the blood-brain barrier in this area.

Immunostaining of TNF-α and TNF-α receptor-1 in the glaucomatous optic nerve head was increased either with POAG or NPG TNF-α is a potent immuno-mediator and pro-inflammatory cytokine that is rapidly upregulated in the brain after injury.[33,34] It is also known as an inducer of apoptotic cell death via TNF-α receptor-1 occupancy.[35] TNF-α has been implicated in the pathogenesis of several diseases of the nervous system such as multiple sclerosis and autoimmune encephalomyelitis and has also been thought to account for axonal degeneration and glial changes observed in the optic nerves of AIDS patients.[36] Although the studies demonstrated that the TNF-α immunostaining was mostly positive in the glial cells of the optic nerve head, TNF-α receptor-1 immunostaining was more prominently positive in nerve bundles located in the prelaminar section of the optic nerve head, which was increased in the glaucomatous eyes. This observation shows that neuronal tissue is an important target for the effects of TNF-α. The findings that the expression of TNF-α and MMPs are both increased in the glaucomatous optic nerve head is not surprising since it is well known that there are interactions between TNF-α and MMPs for the regulation of their secretion and function.[14-18] Increased expression of TNF-α in the glaucomatous optic nerve head therefore demonstrates that this cytokine may play a role in tissue remodeling as a part of the astroglial activation process and/or may participate in tissue injury.

REFERENCES

1. Wax M B, Tezel G, Edward D P. Clinical and histopathological findings of a patient with normal pressure glaucoma. *Arch Ophthalmol*. 1998;116:993–1001.
2. Morrison J C, Dorman-Pease M E, Dunkelberger G R, Quigley H A. Optic nerve head extracellular matrix in primary optic atrophy and experimental glaucoma. *Arch Ophthalmol*. 1990;108:1020–1024.

3. Hernandez M R, Andrzejewska W M, Neufeld A H. Changes in the extracellular matrix of the human optic nerve head in primary open-angle glaucoma. *Am J Ophthalmol.* 1990;109:180–188.
4. Quigley H A, Dorman-Pease M E, Brown A E. Quantitative study of collagen and clastin of the optic nerve head and sclera in human and experimental monkey glaucoma. *Curr Eye Res.* 1991;10:877–888.
5. Hernandez M R. Ultrastructural immunocytochemical analysis of clastin in the human lamina cribrosa: Changes in elastic fibers in primary open-angle glaucoma. *Invest Ophthalmol Vis Sci.* 1992;33:2891–2903.
6. Varela H J, Hernandez M R. Astrocyte responses in human optic nerve head with primary open-angle glaucoma. *J Glaucoma.* 1997;6:303–313.
7. Minckler D S, Spaeth G L. Optic nerve damage in glaucoma. *Surv Ophthalmol.* 1981;26:128–148.
8. Quigley H A, Hohman R M, Addicks E M, Massof R W, Green W R. Morphologic changes in the lamina cribrosa correlated with neural loss in open angle glaucoma. *Am J Ophthalmol.* 1983;95:673–691.
9. Okada Y, Gonoji Y, Nakanishi I, Nagase H, Hayakawa T. Immunohistochemical demonstration of collagenases and tissue inhibitor of metalloproteinases (TIMP) in synovial lining cells of rheumatoid synovium. *Virchows Archiv B Cell Pathol.* 1990;59:305–312.
10. Woessner Jr J F. Matrix metalloproteinases and their inhibitors in connective tissue remodeling. *FASEB J* 1991;5:2145–2154.
11. Backstrom J R, Miller C A: Tokes Z A. Characterization of neural proteinses from Alzheimer-affected and control brain specimens: Identification of calcium-dependent metalloproteinases from the hippocampus. *J Neurochem* 1992;58:983–992.
12. Giraudon P, Buart S, Bernard A, Thomasset N, Belin M F. Extracellular matrix-remodeling metalloproteinases and infection of the central nervous system with retrovirus human T-lymphotropic virus type I (HTLV-I). *Prog Neurobiol.* 1996;49:169–184.
13. Rosenberg G A, Navratil M. Barone F. Feuerstein G. Proteolytic cascade enzymes increase in focal cerebral ischemia in rat. *J Cereb Blood Flow Metabol.* 1996;16:360–366.
14. Ridet J L, Malhotra S K, Privat A, Gage F H. Reactive astrocytes: cellular and molecular cues to biological function. *Trends Neurosci.* 1997;20:570–577.
15. Gottschall P E, Yu X. Cytokines regulate gelatinase A and B (matrix metalloproteinase 2 and 9) activity in cultured rat astrocytes. *J Neurochem.* 1995;64:1513–1520.
16. Gottschall P E, Deb S. Regulation of matrix metalloproteinase expression in astroytes, microglia and neurons. *Neuroimmunomodulation.* 1996;3:69–75.
17. Migita K, Eguchi K, Kawabe Y, et al. TNF-α-mediated expression of membrane-type matrix metalloproteinase in rheumatoid synovial fibroblasts. *Immunology.* 1996;89:553–557.
18. Chandler S, Miller K M, Clements J M, et al. Matrix metalloproteinases, tumor necrosis factor and multiple sclerosis: an overview. *J Neuroimmunol.* 1997;72:155–161.
19. Apodaca G, Rutka J T, Bouhana K, et al. Expression of metalloproteinases and metalloproteinase inhibitors by fetal astrocytes and glioma cells. *Cancer Res.* 1990;50:2322–2329.
20. Eddleston M, Mucke L. Commentary: Molecular profile of reactive astrocytes-implications for their role in neurologic disease. *Neuroscience.* 1993;54:15–36.
21. Romanic A M, Madri J A. Extracellular matrix-degrading proteinases in the nervous system. *Brain Pathol.* 1994;4:145–156.
22. Nakagawa T, Kubota T, Kabuto M et al. Production of matrix metalloproteinases and tissue inhibitor of metalloproteinases-1 by human brain tumors. *J Neurosurg.* 1994;81:69–77.
23. Maeda A, Sobel R A. Matrix metalloproteinases in the normal human central nervous system, microglial nodules, and multiple sclerosis lesions. *J Neuropathol Exp Neurol.* 1996;55:300–309.
24. Raff M C. Glial cell diversification in the rat optic nerve. *Science.* 1989;243:1450–1455.
25. Radany E H, Bernner M, Besnard F, Bigornia V, Bishop J M. Directed establishment of rat brain cell lines with the phenotypic characteristics of type 1 astrocytes. *Proc Natl Acad Sci USA.* 1992;89:6467–6471.
26. Ye H, Hernandez M R. Heterogeneity of astrocytes in human optic nerve head. *J Comp Neurol.* 1995;362:441–452.
27. Hernandez M R, Pena J D. The optic nerve head changes in glaucomatous optic neuropathy. *Arch Ophthalmol.* 1997;115:389–395.
28. Muir D. Metalloproteinase-dependent neurite outgrowth within a synthetic extracellular matrix is induced by nerve growth factor. *Exp Cell Res.* 1994;210:243–252.
29. Nordstrom L A, Lochner J, Yeung W, Ciment G. The metalloproteinase stromelysin-1 (transin) mediates PC12 cell growth cone invasiveness through basal laminae. *Mol Cell Neurosci.* 1995;6:56–68.
30. Schwartz M, Cohen A, Stein-Izsak C, Belkin M. Dichotomy of the glial cell response to axonal injury and regeneration *FASEB J.* 1989;3:2371–2378.
31. Hernandez M R, Igoe F, Neufeld A H. Extracellular matrix of the human optic nerve head. *Am J Ophthalmol.* 1986;102:139–148.
32. Rosenberg G A, Kornfeld M, Estrada E, Kelley R O, Liotta L A, Stetler-Stevenson W G. TIMP-2 reduces proteolytic opening of blood-brain barrier by type IV collagenase. *Brain Res.* 1992;576:203–207.
33. Liu T, Clark R K, McDonnell P C, et al. Tumor necrosis factor-α expression in ischemic neurons. *Stroke.* 1994;25:1481–1488.
34. Barone F C, Arvin B, White R F, et al. Tumor necrosis factor-□. A mediator of focal ischemic brain injury. *Stroke.* 1997;28:1233–1244.
35. Hsu H, Xiong J, Goeddel D V. The TNF receptor 1-associated protein TRADD signals cell death and NF-kappa B activation. *Cell.* 1995;81:495–504.
36. Lin X, Kashima Y, Khan M, Heller K B, Gu X, Sadun A A. An immunohistochemical study of TNF-□ in optic nerves from AIDS patients. *Curr Eye Res.* 1997;16:1064–1068.

EXAMPLE 2

Figure 2:
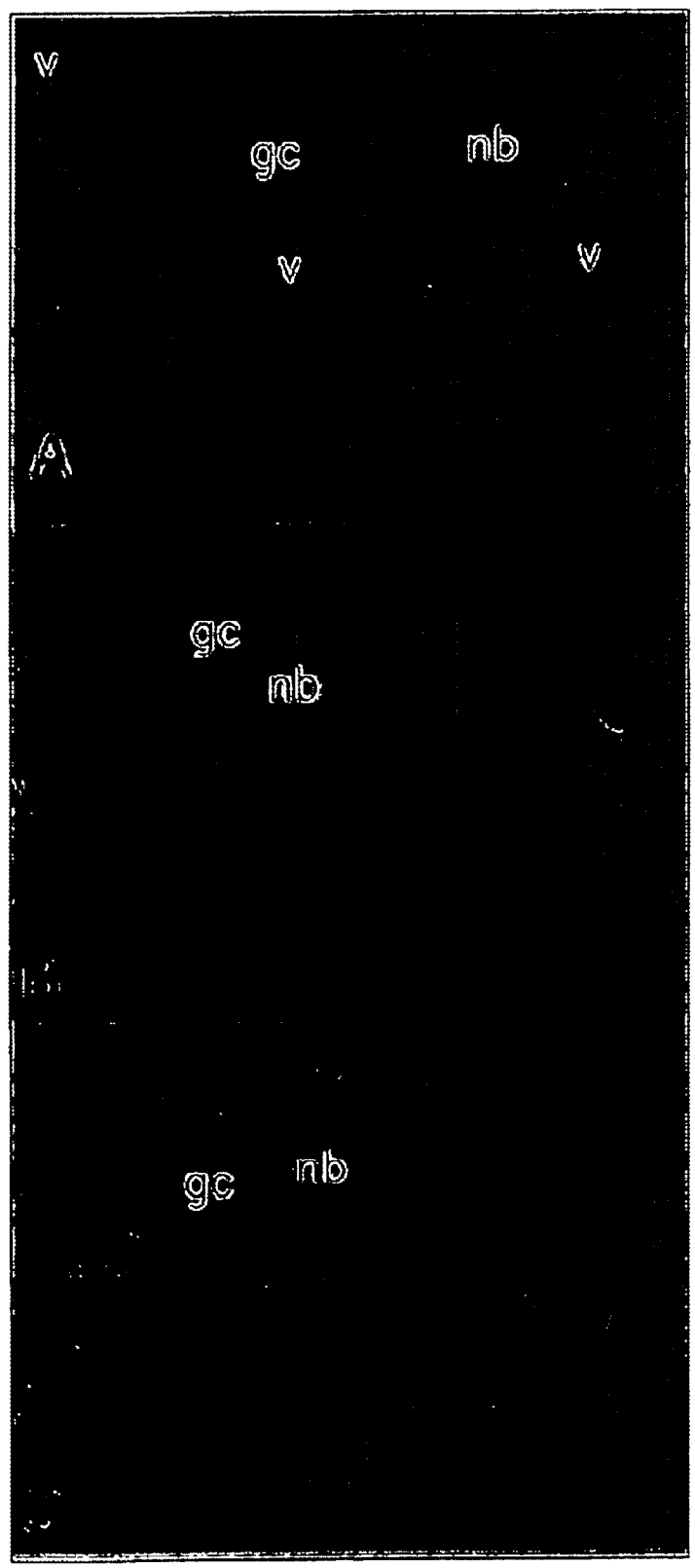
FIG. 2. Immunoperoxidase staining for TNF-α receptor-1 in the human optic nerve head. Faint immunostaining of the prelaminar region of the optic nerve head was noted for TNF-α receptor-1 in the control optic nerve head. (A). Immunostaining was mostly perivascular (v). The intensity of the immunostaining and the number of stained glial cells were greater in the optic nerve heads from patients with primary open angle glaucoma (B) or normal pressure glaucoma (C). Nerve bundles in the prelaminar region also exhibited some immunostaining. (gc, glial column; nb, nerve bundle) (Chromagen, DAB; Nuclear counterstain with Mayer's hematoxylin; original magnification×100).

An Application for the Use of TNF-Alpha Inhibitors Enbrel and Remicade and Other Similar Compounds for the Treatment of Glaucoma Postmortem Immunohistochemistry: In an immunohistochemistry study, antibodies against TNF-α and TNF-α receptor-1 (p55) were used to label optic nerve bead sections from four postmortem eyes from patients with primary open angle glaucoma, 7 eyes from patients with normal pressure glaucoma and 4 eyes from age-matched normal donors. The observations revealed that there is increased expression of TNF-α and its receptor in the glaucomatous optic nerve head. Although the studies demonstrated that the TNF-α immunostaining (FIG. 1) was mostly positive in the glial cells of the optic nerve head, TNF-α receptor-1 immunostaining (FIG. 2) was more prominently positive in nerve bundles located in the prelaminar section of the optic nerve head, which was increased in the glaucomatous eyes. This observation shows that neuronal tissue is an important target for the effects of TNF-α.

Figure 3:
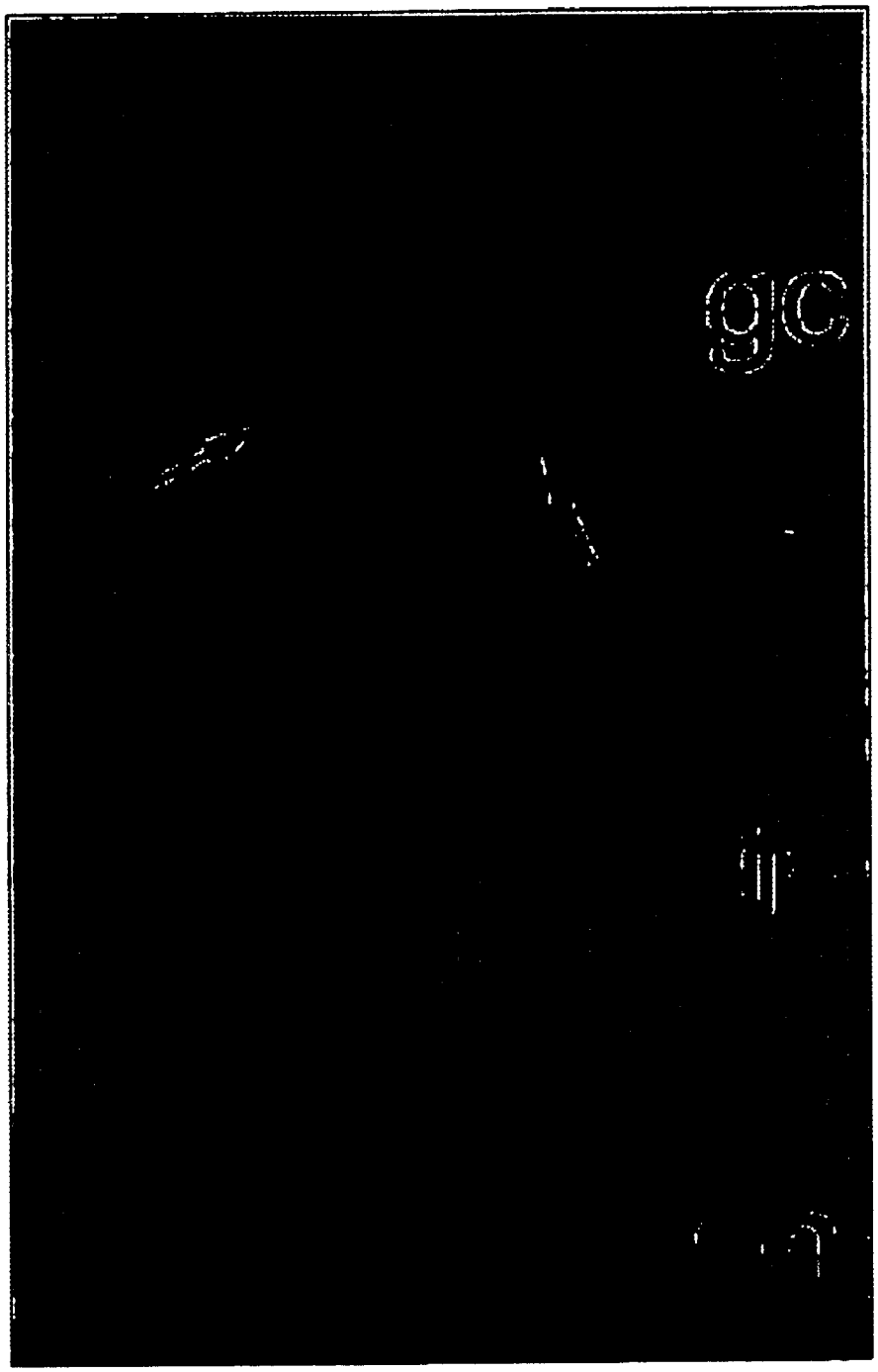
FIG. 3. Immunoperoxidase staining for TNF-α receptor-1 in the retina of an eye with normal pressure glaucoma. Arrows indicate two retinal ganglion cells exhibiting prominent immunostaining for TNF-α receptor-1 (gc, ganglion cells layer; in, inner nuclear layer; on, outer nuclear layer) (Chromagen, DAB; Nuclear counterstain with Mayer's hematoxylin; original magnification×250).

Similar to the observations in optic nerve head, retinal immunostaining of TNF-α and its receptor (FIG. 3) was greater in the retina of glaucomatous eyes either with primary open angle glaucoma or normal pressure glaucoma compared to age-matched normal donors.

Increased expression of TNF-α and its receptor in the glaucomatous optic nerve head and retina demonstrate a role of this cytokine in the neurodegenerative process of glaucoma, which provides a novel therapeutic target for the management of glaucoma.

In vitro Studies: As a part of the experiments to study molecular mechanisms of retinal ganglion cell death, a co-culture system was utilized in which purified human retinal ganglion cells were co-cultured with retinal glial cells grown on tissue culture inserts (Tezel G, Seigel G M, Wax M B. Density-dependent resistance to apoptosis in retinal cells. *Curr Eye Res*. 1999;19:377–388.). This co-cultures provide a good model to study neuron-glia interactions and permits separate assessment of cell survival in neuronal and glial cells. Cultured cells were exposed to different apoptotic stimuli for up to 72 hours that included simulated ischemia or elevated hydrostatic pressure, which are thought to be two primary mechanisms which lead to ganglion cell death in glaucoma.

Figure 4:
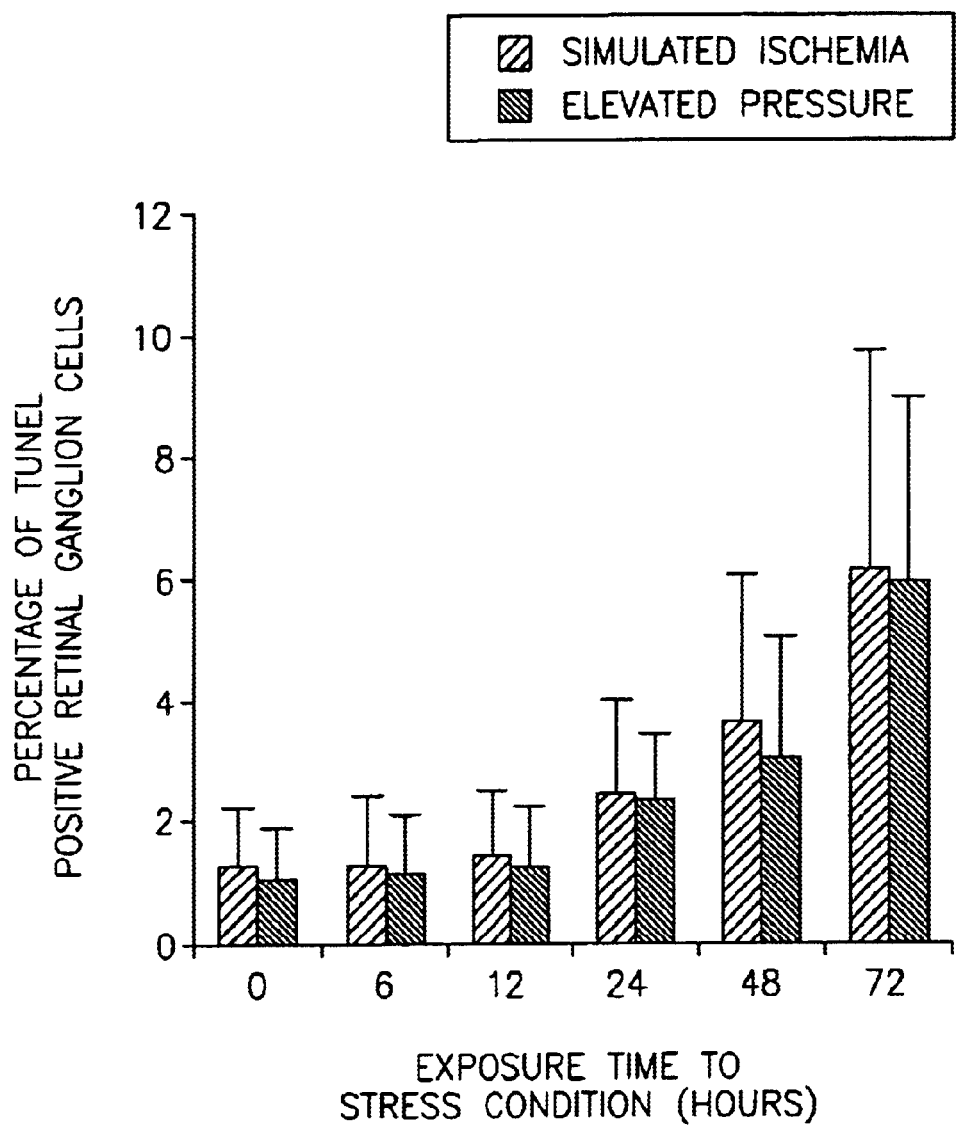
FIG. 4. After exposure of co-cultures to stress conditions, apoptosis rate increased in retinal ganglion cells in a time-dependent manner.
Figure 5:
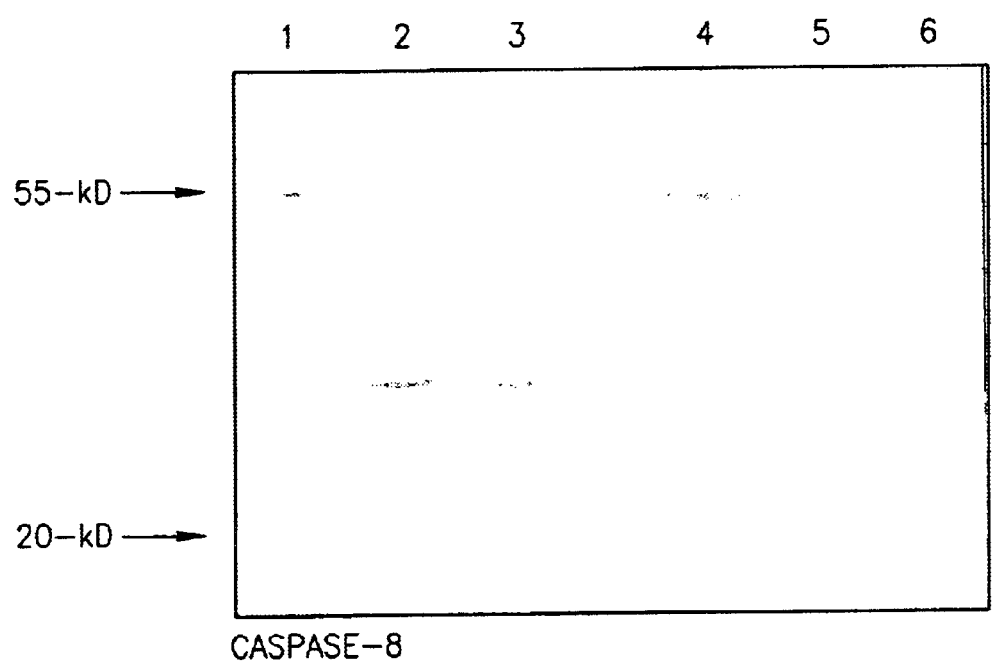
FIG. 5. Examination of caspase-8 activation using western blot analysis in cultured retinal ganglion cells and glial cells. Western blots revealed that after exposure to stress condition, 55-kD immunoreactive band corresponding to caspase-8 cleaved to approximately 30-kD and 20-kD products in retinal ganglion cells. Column 1, retinal ganglion cells incubated under normal condition; column 2, retinal ganglion cells incubated under simulated ischemia; column 3, retinal ganglion cells incubated under elevated pressure; column 4, glial cells incubated under normal condition; column 5, glial cells incubated under simulated ischemia; column 6, glial cells incubated under elevated pressure.

The apoptotic component of cell death was investigated using terminal deoxynucleotidyl transferase-mediated dUTP nick end labeling (TUNEL) technique as well as examination of caspase activation. After exposure to stress conditions, the percentage of TUNEL positive cells increased in retinal ganglion cells in co-cultures with glial cells (FIG. 4). In addition, western blot analysis revealed activation of caspase-8 during the apoptotic process of retinal ganglion cells (FIG. 5) which were subjected to ischemia or elevated hydrostatic pressure.

Figure 6:
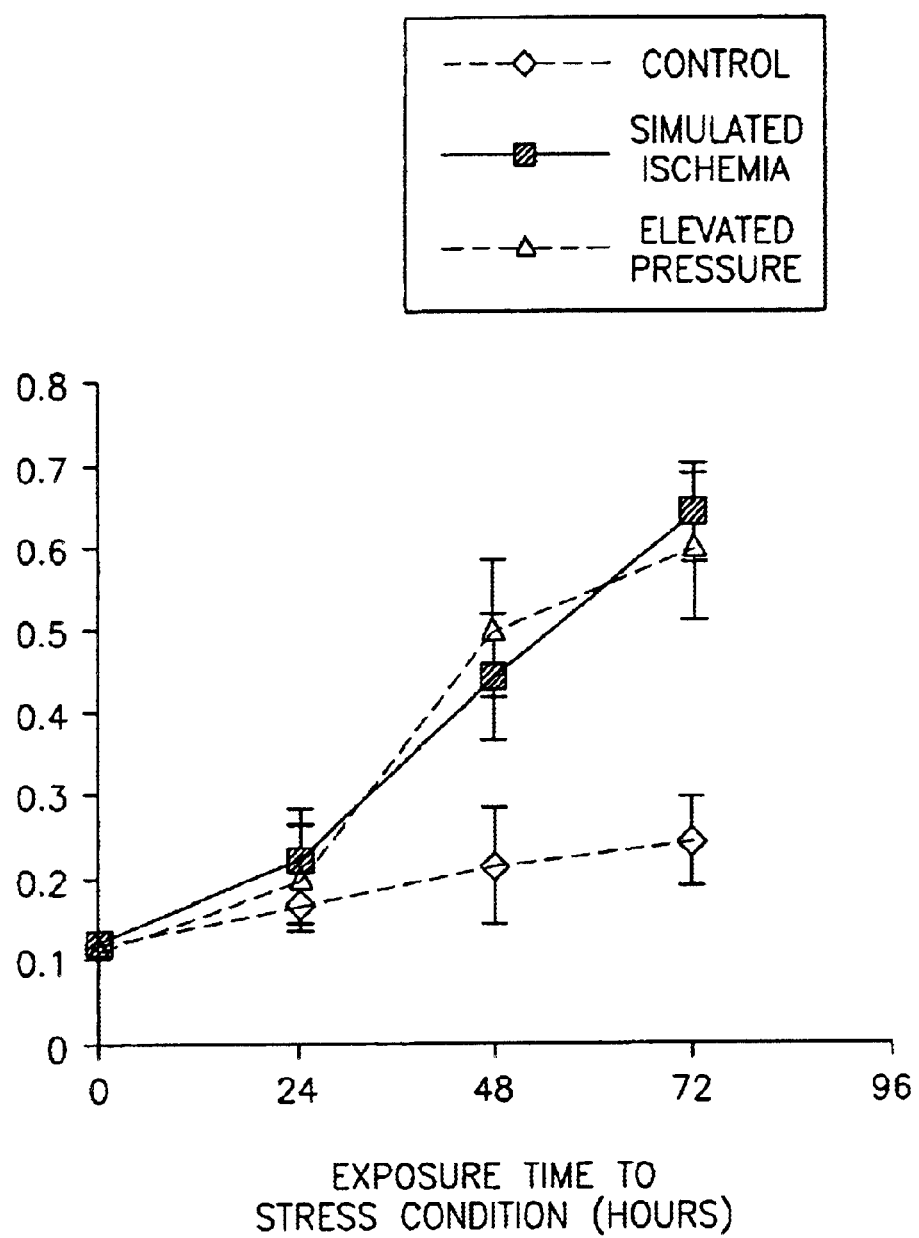
FIG. 6. After exposure of co-cultures to stress conditions, TNF-α in conditioned medium in a time dependent manner.

Western blot analysis also revealed increased expression of TNF-α in glial cells. In addition, an enzyme-linked immunosorbent assay was performed to measure levels of TNF-α in the conditioned medium. The level of TNF-α in the conditioned medium was higher in co-cultures incubated under stress conditions compared to that incubated under normal condition (FIG. 6).

These observations demonstrate that glial cells exposed to simulated ischemia or elevated hydrostatic pressure have a neurotoxic effect on retinal ganglion cells, due to increased production of apoptosis-promoting substances, which include TNF-α. Accordingly, stress conditions such as ischemia and/or elevated intraocular pressure results in glial "activation" of astrocytes and microglia that surround the retinal ganglion cell fibers both in the retina (microglia) and in the specialized structure of the sclera called the lamina cribrosa (microglia and astrocytyes), through which retinal ganglion cells pass as they leave the eye to form the optic nerve.

In vivo studies: Also a rat model of high pressure glaucoma was used (Shareef S R, Garcia-Valenzuela E, Salierno A, Walsh J, Sharma S C. *Exp Eye Res*. 1995;61:379–382). After unilateral elevation of intraocular pressure in rats by cautery of three episcleral vessels, retinal expression of caspase-8 was increased. The observation of caspase-8 activation during both in vitro and in vivo experiments further demonstrates the involvement of TNF-α in the apoptosis of retinal ganglion cells.

EXAMPLE 3

Increased Production of TNF-□ by Glial Cells Exposed to Simulated Ischemia or Elevated Hydrostatic Pressure Induces Apoptosis in Co-cultured Retinal Ganglion Cells Materials and Methods Retinal ganglion cell cultures. Primary cultures of retinal ganglion cells were derived from newborn rat retinas using a protocol similar to that recently described[70]. All experiments were performed in accordance with the ARVO Statement for the Use of Animals in Ophthalmic and Vision Research and were approved by The Animal Studies Committee of Washington University. Five to seven days old Sprague-Dawley rats were anesthetized and their eyes were enucleated. The eyes were rinsed with $CO_2$-independent culture medium (Gibco, Grand Island, N.Y.) and retinas were mechanically dissected under a microscope. To prepare retinal cell suspensions, tissues were dissociated in Eagles's minimum essential medium containing 20 U/ml papain, 1 mM L-cystein 0.5 mM EDTA and DNase (0.005%) (Worthington, Lakewood, N.J.) at 37° C. for 40 minutes. Then, retinas were rinsed in an inhibitor solution containing Eagle's minimum essential medium, ovomucoid (0.2%) (US Biological, Swampscott, Mass.), DNAase (0.04%) and bovine serum albumin (0.1%) (Sigma, St. Louis, Mo.). At the end of treatment period, tissues were triturated through a 1 ml plastic pipette to yield a suspension of single cells. The retinal cells were spun at 400 g for 10 minutes, resuspended in Eagle's minimum essential medium containing bovine serum albumin (0.05%) and incubated in a tissue culture incubator until their immediate use for subsequent separation by immunomagnetic selection[71,72].

Immunomagnetic selection of the retinal ganglion cells was performed using magnetic, 2.8±0.2 um diameter, polystyrene beads coated with biotinylated rat monoclonal antibody against mouse $IgG_1$ (Dynal, Oslo, Norway) in a two step process. In the first step, after washing with phosphate buffered saline solution containing 0.1% bovine serum albumin, $1\times10^7$ beads/ml were added to monoclonal antibody against macrophage surface antigens (100 ug/ml) (Sigma). After incubation at room temperature on a rotator for 30 minutes, beads were washed using a specially designed magnet (Dynal). Coated beats were incubated with retinal cell suspension with gentle rotation for 15 minutes and then removed from the cell suspension to remove bound macrophages. As a second step, fresh magnetic beads were added to monoclonal antibody ($IgG_1$) specific to Thy-1.1 (Chemicon, Temecula, Calif.) to obtain 100 □g/ml of final concentration. After incubation at room temperature for 30 minutes and washing, the coated beads were incubated with the macrophage-depleted retinal cell suspension for 15 minutes. Since the monoclonal antibody was attached to beads via streptavidin and a DNA linker, the attached cells were separated from beads by incubation with DNase releasing buffer (50 U/ul) at 37° C. for 15 minutes. The cells were then seeded on extracellular matrix-coated 24-well plates (Fisher, Pittsburgh, Pa.) at a density of $4\times10^4$ cells/well and co-cultured with glial cells. Cultures were incubated in a tissue culture incubator with humidified atmosphere of 5% $CO_2$ and 95% air at 37° C.

A retinal glial cell line was prepared using retinal cells depleted for microglial and ganglion cells following the magnetic selection process described above. After loss of residual neuronal cells by two or three cycles of replating, these cultures contained essentially glial cells as previously described[73], which were identified as astrocytes and Muller glial cells as presented in the results section. The retinal glial cells were seeded on tissue culture inserts (Fisher) at a density of $3 \times 10^4$ cells/well and placed in the wells in which retinal ganglion cells were seeded. These inserts contain 0.4 um thickness polyethylene terephthalate membrane with $1.6 \times 10^6$ pores/cm$^2$ and allow transport of secreted molecules while preventing cell migration.

The serum-free culture medium was prepared using B27-supplemented Neurobasal™ (Gibco, Grand Island, N.Y.) as previously described[17,74]. The medium also contained bovine serum albumine (100 ug/ml), progesteron (60 ng/ml), insuline (5 ug/ml), pryruvate (1 mM), glutamine (1 mM), putrescine (16 □g/ml), sodium selenite (40 ng/ml), transferrin (100 ug/ml), triiodo-thyronine (30 ng/ml), BDNF (50 ng/ml), CNTF (20 ng/ml), bFGF (10 ng/ml), forskolin (5 uM), inosine (100 uM) and antibiotics[75]. All supplements were purchased from Sigma.

Retrograde labeling of retinal ganglion cells. Under general anesthesia using a mixture of 80 mg/kg ketamine (Fort Dodge Laboratories, Fort Dodge, Iowa) and 12 mg/kg xylazine (Butler, Columbus, Ohio) given intraperitoneally, and immobilization of rats in a stereotaxic apparatus, bilateral microinjections of Fluoro-Gold (Fluorochrome Inc., Englewood, Colo.) (1.5 ul of a 5% solution of Fluoro-Gold in 0.9% sodium chloride) into the superior colliculi were performed according to the previously described methods[76]. One week after Fluoro-Gold application, the retinas were dissected and dissociated. After selection of retinal ganglion cells using immunomagnetic method, selected and un-selected cells were examined by flow cytometry, after double immunolabeling of Fluoro-Gold and Thy-1.1.

Flow cytometry. Retinal cells were fixed with 2% paraformaldehyde solution for 20 minutes at room temperature. After centrifuge and resuspension of the cells, they were permeabilized in Triton X-100 (0.4% in phosphate-buffered saline solution) for 30 minutes. Washed cells were then incubated with a mixture of rabbit antibody against Fluoro-Gold (Fluorochrome Inc.) and mouse antibody against Thy-1.1 at 1:100 dilution for 30 minutes. After washing, the cells were incubated with a mixture of FITC- and Cy3-conjugated secondary antibodies (Sigma) for another 30 minutes. The cells were then washed, resuspended at $10^6$ cells/ml and counted using a FACScan flow cytometer/CELLQuest Software system (Becton-Dickinson, San Jose, Calif.).

Study Design. The retinal ganglion cells exhibiting contact of the neuritic processes and glial cells grown to approximate confluence were incubated under stress conditions or normal condition. For simulated ischemia, cells were exposed to reduced oxygen tensions in a medium lacking glucose. Hypoxia was maintained by placing the cultures in a dedicated culture incubator with a controlled flow of 95% $N_2$/5% $CO_2$. A closed pressurized chamber equipped with a manometer was used to expose cells to elevated hydrostatic pressure. The pressure was elevated to 50 mmHg. The chamber was placed in a regular tissue culture incubator at 37° C. To examine the time course of cellular responses, the simulated ischemia or elevated pressure was maintained 6, 12, 24, 48 or 72 hours. Control cells from identical passage of cells were simultaneously incubated in a regular tissue culture incubator at 95% air/5% $CO_2$ and 37° C. To examine glial sources of noxious insults on retinal ganglion cells, conditioned medium was collected from glial cells cultured alone following their incubation in the presence or absence of stress conditions for 72 hours. Retinal ganglion cells cultured alone were then incubated with the conditioned medium of glial cells for 24 hours.

In addition, to examine the role of TNF-α and NO on cell survival, incubations under stress conditions were performed in the presence or absence of specific inhibitors. A neutralizing antibody (AF510NA) was used to inhibit TNF-α activity (R&D Systems, Minneapolis, Minn.). The ability of this antibody to neutralize the bioactivity of recombinant rat TNF-α in L-929 cell line in the presence of actinomycin D revealed that the Neutralization Dose$_{50}$ was approximately 0.3–0.9 ug/ml in the presence of 0.025 ng/ml of recombinant rat TNF-α. The neutralizing antibody of TNF-α activity was neuroprotective, in in Vitro, or in Vivo experiments[77-79]. In addition, [N-(3-(aminomethyl)benzyl) acetamidine. dihydrochloride] (1400W) (Alexis, San Diego, Calif.), a selective inhibitor of iNOS, was used to inhibit inducible synthesis of NO[80]. 10 ug/ml of the neutralizing antibody of TNF-α and 2.5 uM of the iNOS inhibitor, 1400W was used, since these were optimum conditions to inhibit TNF-α and iNOS, respectively, in the co-cultures based on concentration-response experiments. At the end of the incubation period, the cells were immediately subjected to experiments described below, which were repeated at least three times for each condition.

The viability of the cells was determined with the Live/Dead Kit (Molecular Probes, Eugene, Oreg.) which contains calcein AM and ethidium homodimer[81]. Calcein AM is a cell-permeable fluorogenic esterase substrate. The kit relies on the intracellular esterase activity within living cells to hydrolyze calcein AM to a green fluorescent product, calcein. In dead cells ethidium can easily pass through the compromised plasma and nuclear membranes and attach to the DNA, yielding red fluorescence. Cells were counted at least 10 random fields of each well at 200×magnification (~150 ganglion cell per well) using a fluorescence microscope (Olympus, Tokyo, Japan). The viability of the cells was expressed as the average ratio of esterase (+) cells to the total number of cells multiplied by 100.

Morphologic analysis of apoptosis. An in situ cell death detection kit (Boehringer Mannheim, Mannheim, Germany) was used to identify the apoptotic cells by terminal deoxy-nucleotidyl transferase-mediated dUTP nick end labeling (TUNEL) technique[82]. Briefly, after fixation, permeabilization and blocking steps, air-dried cells were incubated with a mixture of fluorescein-labeled nucleotides and terminal deoxynucleotidyl transferase for 1 hour. Terminal deoxynucleotidyl transferase catalyzes the polymerization of labeled nucleotides to free 3'-OH terminals of DNA fragments. Cells incubated with fluorescein-labeled nucleotide mixture without the presence of terminal deoxynucleotidyl transferase served as a negative control. Cells previously treated with Dnase I (1 mg/ml) to induce breaks in the DNA strands served as a positive control. TUNEL positive cells were counted in triplicate wells under fluorescence microscope and the percentage of apoptosis was calculated using the total number of cells in these wells.

Western blotting. After washing the cells with phosphate-buffered saline solution, they were lysed in sample buffer (1% SDS, 100 mM dTT, 60 mM Tris, pH 6.8, 0.001% bromophenol blue). Protein concentrations were determined using the BCA method (Sigma). The samples were boiled for 5 minutes before subjecting them to electrophoresis.

Samples were separated by electrophoresis in 10–15% sodium dodecyl sulfate polyacrylamide gels at 160-V for 1 hour and electrophoretically transferred to polyvinylidene fluoride membranes (Millipore, Marlboro, Mass.) using a semi-dry transfer system (BioRad, Hercules, Calif.). After transfer, membranes were blocked in a buffer (50 nM Tris HCl, 154 mM NaCl, 0.1% Tween-20, pH 7.5) containing 5% non-fat dry milk for 1 hour, then overnight in the same buffer containing a dilution of primary antibody and sodium azide. Primary antibodies were monoclonal antibodies to TNF-□ (R&D Systems), isotypes of NOS (neuronal NOS and iNOS) (Transduction Laboratories, Lexington, Ky.) or caspase-8, or polyclonal antibody to caspase-3 (Pharmigen, San Diego, Calif.) and were used at a dilution of 1:000. After several washes and the second blocking for 20 minutes, the membranes were incubated with a dilution of secondary antibodies conjugated with horse-radish peroxidase (Fisher Scientific, Pittsburgh, Pa.) at 1:2000 for 1 hour. Immunoreactive bands were visualized by enhanced chemiluminescence using commercial reagents (Amersham Life Science, Arlington Heights, Ill.).

In situ examination of caspase activity. Caspase-3-like activity was examined after staining with Phiphilux-$G_6D_2$ (Alexis, San Diego, Calif.). Phiphilux-$G_6D_2$ is a cell permeable, fluorogenic substrate that is cleaved in a DEVD-dependent manner to produce rhodamine molecules and can be used to detect caspase-3-like activity in living cells[83]. For staining, washed cells were incubated with 10 uM of substrate solution for 20 minutes at 37° C. Rhodamine fluorescence was visualized under a fluorescence microscope.

Immunocytochemistry. Cells were washed in phosphate-buffered saline solution, fixed with 4% paraformaldehyde solution for 30 minutes at room temperature. After washing, they were permeabilized with 0.1% Triton X-100 in 0.1% sodium citrate solution on ice for 4 minutes. The cells were then treated with 3% bovine serum albumin for 30 minutes to block non-specific binding sites. Triplicate wells were incubated with monoclonal antibodies against TNF-□ (R&D Systems) or isotypes of NOS (neuronal NOS and iNOS) (Transduction Laboratories) at 37° C. for 2 hours. Samples were then washed and incubated with appropriate second antibodies conjugated with Cy3 (Sigma). After washing they were examined using a fluorescence microscope.

For examination of the purity of cultures, the cells were double-immunolabeled using specific cell markers. For double immunofluorescence labeling, following fixation, permeabilization and blocking steps, the cultures were incubated with a mixture of two antibodies (one rabbit and one mouse antibody) against Thy-1.1, neurofilament protein, glial fibrillary acidic protein or S-100 protein (Sigma) at 1:100 dilution for 30 minutes. After washing, the cells were incubated with a mixture of Cy3 and FITC-conjugated secondary antibodies (Sigma) for another 30 minutes. Negative controls were performed by replacing the primary antibody with non-immune serum or by incubating the cells with the each primary antibody followed by the inappropriate secondary antibody to determine that each secondary antibody was specific to the species it was made against. The cultures were then examined using a fluorescence microscope.

Enzyme-linked immunosorbent assay (ELISA). A kit to measure TNF-α levels in conditioned medium by quantitative sandwich ELISA technique (R&D Systems) was used. Conditioned medium was incubated in microwells coated with monoclonal antibody specific for rat TNF-α After washing, horseradish peroxidase-conjugated polyclonal antibody specific for rat TNF-α is added to the wells. Following a wash, a substrate solution containing hydrogen peroxide and tetramethylbenzidine was added. The enzyme reaction was terminated by addition of hydrochloric acid solution and absorbance was measured at 450 nm. Using a standard curve prepared from seven dilutions of recombinant rat TNF-α concentrations of TNF-α in conditioned medium was calculated. The sensitivity was less than 5 pg/ml.

Colorimetric assay. To measure breakdown products of NO in conditioned medium a colorimetric assay kit (R&D Systems) was used. This assay determined NO based on the enzymatic conversion of nitrate to nitrite by nitrate reductase. The reaction was followed by a calorimetric detection of nitrite as an azo dye product of the Griess reaction. As an additional step, lactate dehydrogenase and pyruvic acid was used prior to color formation to oxidize the excess of NADPH since NADPH, an essential cofactor for the function of NOS enzyme, interferes with the chemistry of Griess reagents. Since the relative levels of nitrate and nitrite-can vary substantially depending on the ambient conditions and redox state of the biological fluids, for most accurate determination of total NO production both nitrate and nitrite levels were measured. The absorbance was read at 540 nm and the concentrations of breakdown products of NO were calculated using a standard curve. The sensitivity of the nitrite assay was less than 0.22 umol/L and the sensitivity of the nitrate assay was less than 0.54 umol/L.

RESULTS

Cell morphology and viability: Retinal ganglion cells were identified on the basis of retrograde labeling with Fluoro-Gold, morphology and expression of cell markers. Following retrograde labeling with Fluoro-Gold and selection of retina ganglion cells using an immunomagnetic separation method, the cells were immunolabeled by antibodies against Fluoro-Gold and Thy-1.1. Using flow cytometry, the immunolabeling by Fluoro-Gold and Thy-1.1 antibodies was co-localized in more than 90% of these cells, while more than 95% of the cells were positive for Thy-1.1 (FIG. 7a). Cells unselected by sorting were negative for both Fluoro-Gold and Thy-1.1 (FIG. 1b).

Figure 7:
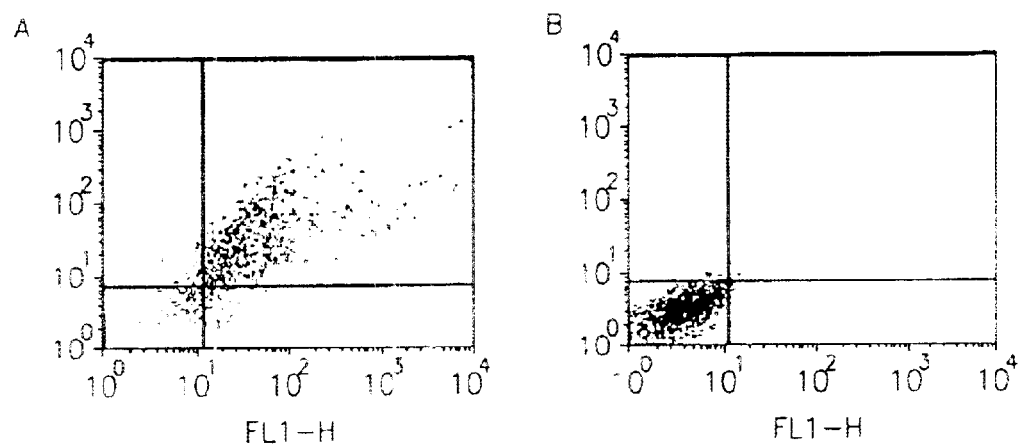
FIG. 7. Cultured retinal cells. Following retrograde labeling by Fluoro-Gold and selection of retinal ganglion cells using an immunomagnetic separation method, the selected cells were immunolabeled using antibodies against Fluoro-Gold and Thy-1.1, and examined using flow cytometry. (a) immunolabeling using Fluoro-Gold (FL1-H) and Thy-1.1 (FL3-H) antibodies was co-localized in more than 90% of these cells, while more than 95% of these cells were positive for Thy-1.1. (b) Unselected cells were negative for both Fluoro-Gold (FL1-H) and Thy-1.1 (FL3-H). Cultured retinal ganglion cells had round or oval cell bodies with a diameter of 10–20 □m, phase-bright appearance and branched neuritis of uniform caliber and varying length. (c) A retinal ganglion cell derived from newborn rat retina. (d) Fluorescence microscope image of the retinal ganglion cell shown in panel (c) after labeling for neurofilament protein. (e) Fluorescence microscope image of the retinal ganglion cell shown in panel (c) after labeling for Thy-1.1. (f) Glial cells derived from newborn rat retina. (g) Fluorescence microscope image of the retinal glial cells shown in panel (i) after labeling for glial fibrillary acidic protein. (h) Fluorescence microscope image of the retinal glial cells shown in panel (i) after labeling for S-100 Magnification bar; c through e, 20 □m; f through h, 60 μm.
Figure 7:
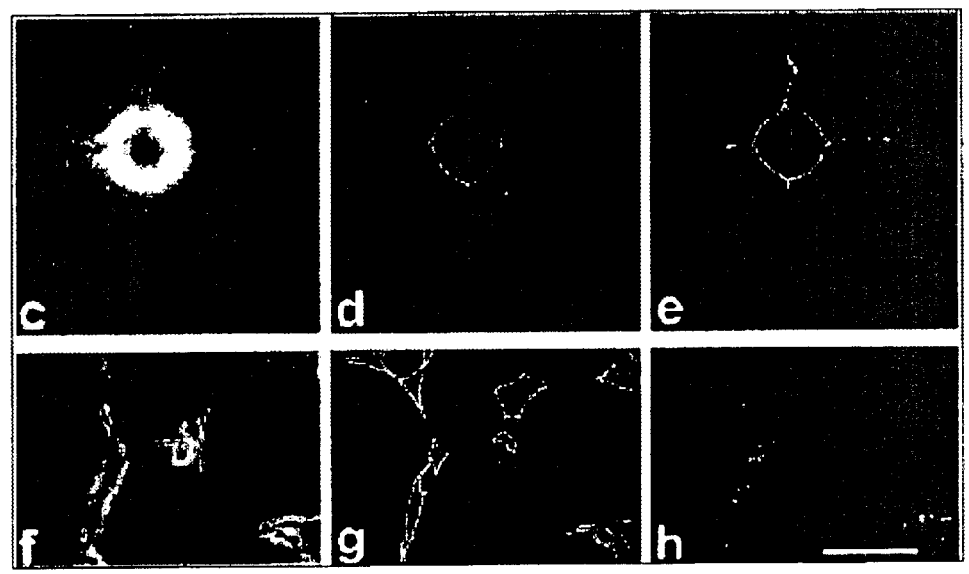

Cultured retinal ganglion cells had round or oval cell bodies with a diameter of 10–20 □m, a phase-bright appearance and branched neurites of uniform caliber and varying length (FIG. 7c) as previously identified[17]. In addition, the purity of cultured retinal cells was examined using immunolabeling for specific markers. The retinal ganglion cells were homogenously positive for Thy-1.1 and neurofilament protein, but negative for glial markers. Glial cells were homogenously labeled for glial fibrillary acidic protein, selectively labeled for S-100, but unlabeled for neuronal markers (FIG. 7).

At the beginning of the incubation of co-cultures under stress conditions, the percentage of living retinal ganglion cells and glial cells were 96.69±1.6% and 97.84±1.9%, respectively. The cell viability decreased to 69.69±2.0% and 76.64±1.9% in retinal ganglion cells after 72 hours of incubation in the presence of simulated ischemia or elevated hydrostatic pressure, respectively. However, the viability of glial cells was 96.24±2.1% at the end of incubation period either under simulated ischemia or elevated hydrostatic pressure.

Figure 8:
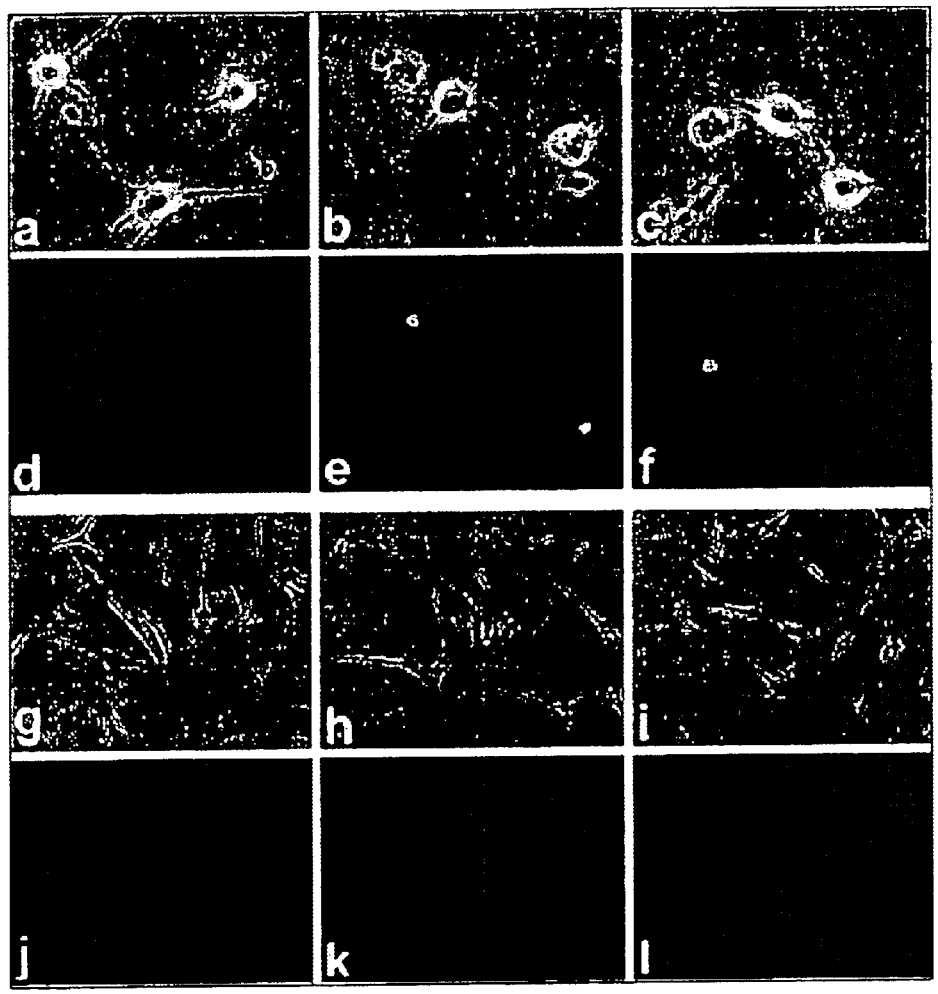
FIG. 8. Morphologic analysis of apoptotic cell death in co-cultures of retinal ganglion cells and glial cells. Phase contrast microscope image of retinal ganglion cells incubated under normal condition (a), simulated ischemia (b) or elevated hydrostatic pressure (c) for 72 hours. Fluorescence microscope images of TUNEL in panels (d), (e) and (f) correspond to retinal ganglion cells seen in panels (a), (b) and (c), respectively. Phase contrast microscope image of glial cells incubated under normal condition (g), simulated ischemia (h) or under elevated hydrostatic pressure (i) for 72 hours. Fluorescence microscope images of TUNEL in panels (j), (k) and (l) correspond to glial cells seen in panels (g), (h) and (l), respectively. Following incubation of co-cultures under stress conditions, apoptosis was induced in retinal ganglion cells while there was no evidence of apoptosis in glial cells.

Induction of apoptosis in retinal ganglion cells in co-cultures exposed to simulated ischemia or elevated hydrostatic pressure: Apoptosis was induced in retinal ganglion cells following incubation of co-cultures in the presence of simulated ischemia or elevated hydrostatic pressure for as long as 72 hours. Specific morphologic changes of apoptotic cell death included cell body shrinkage and compaction of the nucleus (FIGS. 8a–c). In addition, apoptotic cell death was examined using TUNEL technique. The apoptotic retinal ganglion cells exhibited bright labeling of fragmented nuclear DNA by TUNEL technique (FIGS. 8d–f). However, there was no evidence of apoptosis in glial cells in co-cultures incubated under stress conditions using either morphologic examination or TUNEL technique (FIGS. 8g–l).

Figure 9A:
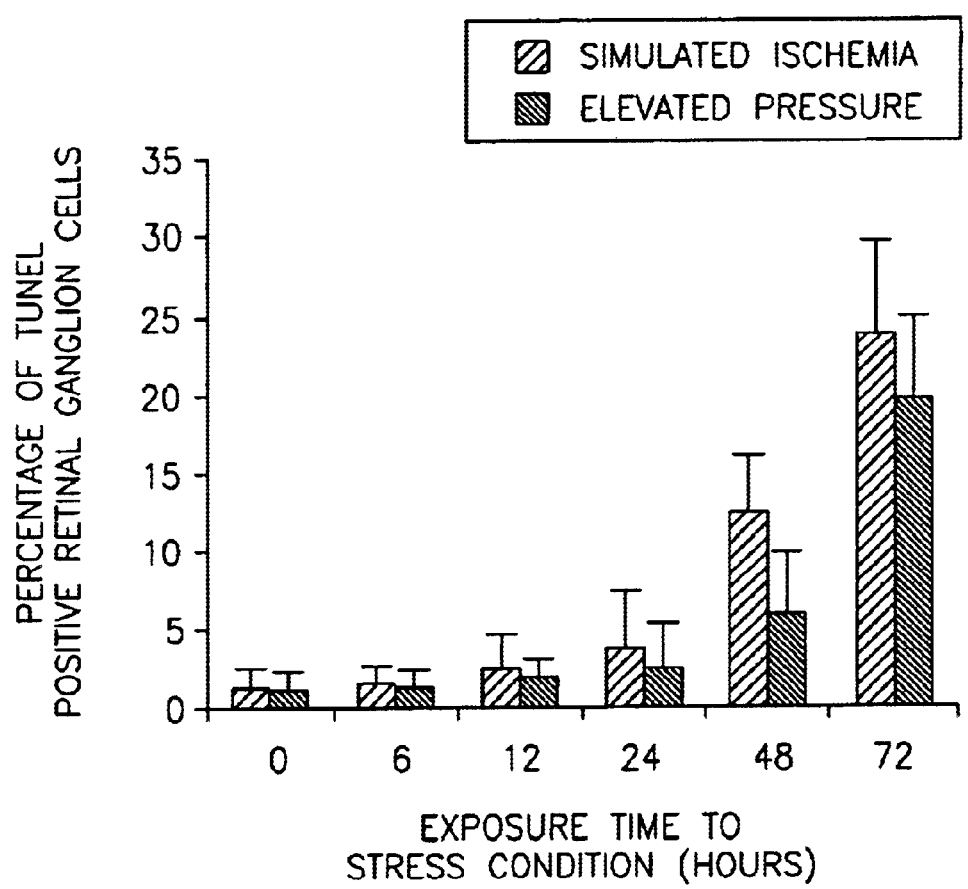
FIG. 9. (a) Quantitative analysis of positive TUNEL in retinal ganglion cells in co-cultures incubated under simulated ischemia or elevated hydrostatic pressure. (b) Quantitative analysis of positive TUNEL in retinal ganglion cells following passive transfer experiments. Conditioned medium of glial cells cultured alone was collected following their incubation in the presence or absence of simulated ischemia or elevated hydrostatic pressure for 72 hours. Retinal ganglion cells cultured alone were then incubated with the glial conditioned medium for 24 hours.
Figure 9B:
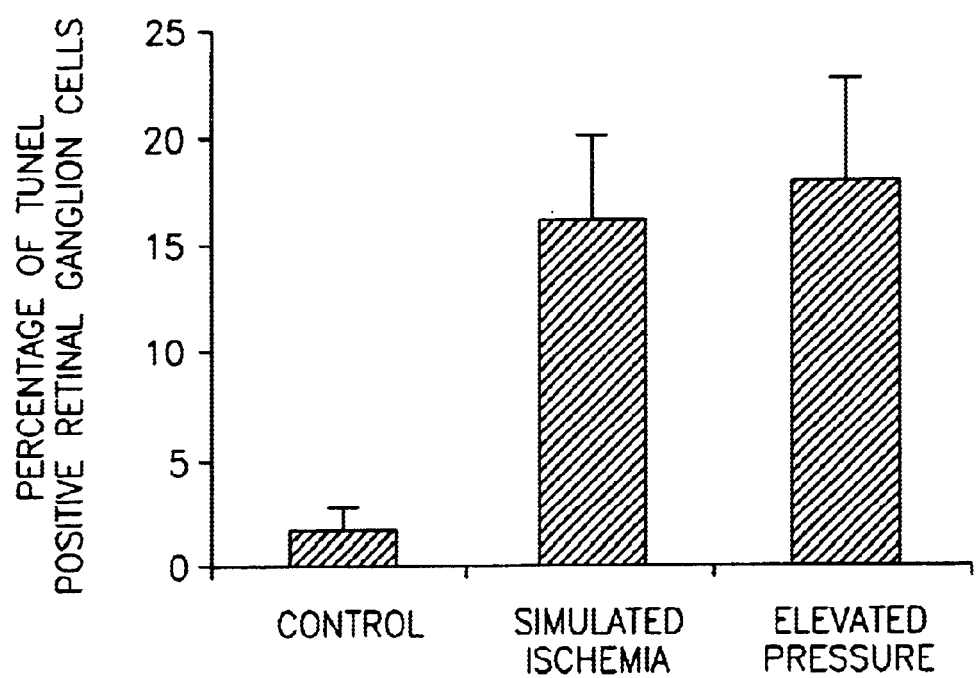

Quantitative examination of co-cultures following incubation under stress conditions revealed that the percentage of positive TUNEL was approximately three times greater in retinal ganglion cells co-cultured with glial cells compared to retinal ganglion cells cultured alone. Following incubation under stress conditions for 72 hours, more than 20% of the retinal ganglion exhibited positive TUNEL. However, in the retinal ganglion cells cultured alone the rate of positive TUNEL was less than 7%. Following incubation under stress conditions, apoptosis was induced in retinal ganglion cells in co-cultures in a time-dependent manner (FIG. 9a). While the rate of positive TUNEL was 24.10±6.0% and 19.90±5.4% in retinal ganglion cells in co-cultures exposed to simulated ischemia or elevated hydrostatic pressure for 72 hours, respectively, retinal ganglion cells in control cultures incubated under normal condition exhibited apoptosis in less than 2% of the cell population (Mann-Whitney U test, p=0.017, p=0.023, respectively). However, the percentage of positive TUNEL was virtually absent in glial cells incubated in the absence or presence of stress conditions (0.94±0.6% and 1.12±1.0%, respectively) (p>0.05 for both condition).

In addition, passive transfer experiments were performed to examine the glial source of noxious insults on retinal ganglion cells. For this purpose, conditioned medium of glial cells cultured alone was collected following their incubation in the presence or absence of simulated ischemia or elevated hydrostatic pressure for 72 hours. Retinal ganglion cells cultured alone were then incubated with the glial conditioned medium for 24 hours. The TUNEL was positive in approximately 17% of retinal ganglion cells incubated with the conditioned medium of stressed glial cells, while less than 2% of retinal ganglion cells exhibited positive TUNEL in cultures incubated with the conditioned medium of glial cells incubated under normal condition (Mann-Whitney U test, p=0.04 and p=0.02 for simulated ischemia and elevated hydrostatic pressure, respectively) (FIG. 3b).

Figure 10:
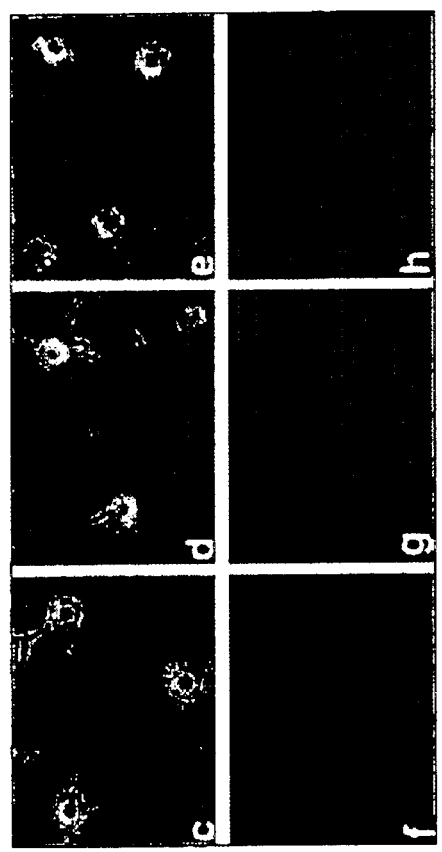
FIG. 10. Examination of caspase activity in co-cultures incubated under simulated ischemia or elevated hydrostatic pressure. (a) Western blot analysis of caspase-8 expression in co-cultures. (b) Western blot analysis of caspase: 3 expression co-cultures. Column 1, control retinal ganglion cells; column 2, retinal ganglion cells incubated under simulated ischemia for 72 hours; column 3, retinal ganglion cells incubated under elevated hydrostatic pressure for 72 hours; column 4, control glial cells; column 5, glial cells incubated under simulated ischemia for 72 hours; column 6, glial cells incubated under elevated hydrostatic pressure for 72 hours. Western blots revealed that 55-kD immunoreactive band corresponding to caspase-8 cleaved to 30-kD and 20-kD products in retinal ganglion cells incubated under stress conditions. In addition, 32-kD pro-enzyme caspase-3 cleaved to a 17-kD active subunit in retinal ganglion cells. No cleavage of caspase-8 or caspase-3 was detected using the extracts of glial cells. Caspase activation was also examined, in Situ, using Phiphilux-$G_6D_2$. (c) Retinal ganglion cells incubated under normal condition (d), simulated ischemia (e) or elevated hydrostatic pressure (f) for 72 hours. Fluorescence microscope images seen in panels (f), (g) and (h) correspond to phase contrast images of the retinal ganglion cells seen in panels (c), (d) and (e), respectively. Rhodamine fluorescence (red) indicates caspase-3-like activity in retinal ganglion cells incubated under stress conditions.
Figure 10:
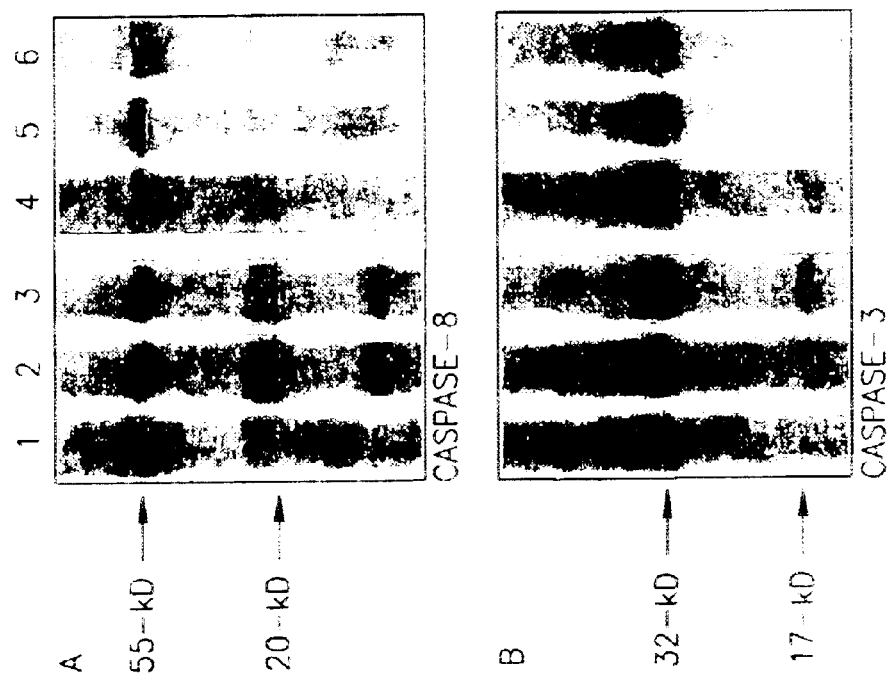

Caspase activation accompanying retinal ganglion cell apoptosis: To examine caspase activation, lysates of retinal cells were used in western blotting. Western blot analysis demonstrated cleavage of caspase-8 and caspase-3 in retinal ganglion cells after exposure of co-cultures to simulated ischemia or elevated hydrostatic pressure. Western blots using the lysates of retinal ganglion cells incubated under stress conditions revealed a 55-kD immunoreactive band corresponding to caspase-8 and approximately 30-kD and 20-kD cleaved products. The presence of caspase-3 activation was assessed by the observation of 17-kD subunit that was derived from the cleavage of 32-kD pro-enzyme caspase-3. No cleavage of caspase-8 or caspase-3 was detected using the lysates of glial cells incubated under stress conditions (FIGS. 10a and b).

In Situ examination of caspase activity was performed. Using the fluorogenic substrate, Phiphilux-G6D2, caspase-3-like activity was detected in living retinal ganglion cells exposed to simulated ischemia or elevated hydrostatic pressure (FIGS. 10c–h).

Figure 11:
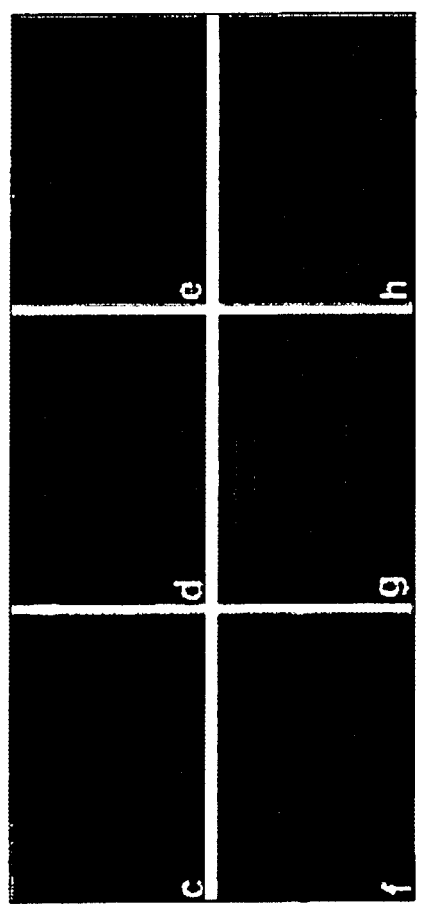
FIG. 11. Examination of TNF-α and iNOS expression in co-cultures incubated under simulated ischemia or elevated hydrostatic pressure. Both western blot analysis (a and b) and immunocytochemistry (c through h) revealed increased expression of TNFα and iNOS in glial cells and not in retinal ganglion cells in co-cultures incubated under stress conditions. (a) Western blot analysis of TNF-□ expression. (b) Western blot analysis of iNOS expression. Column 1, control retinal ganglion cells; column 2, retinal ganglion cells incubated under simulated ischemia for 72 hours; column 3, retinal ganglion cells incubated under elevated hydrostatic pressure for 72 hours; column 4, control glial cells, column 5, glial cells incubated under simulated ischemia for 72 hours; column 6, glial cells incubated under elevated hydrostatic pressure for 72 hours. TNF-α expression in glial cells incubated under normal condition (c), under simulated ischemia for 72 hours (d) or under elevated hydrostatic pressure for 72 hours (e). iNOS expression in glial cells incubated under normal condition (f), under simulated ischemia for 72 hours (g) or under elevated hydrostatic pressure for 72 hours (b).
Figure 11:
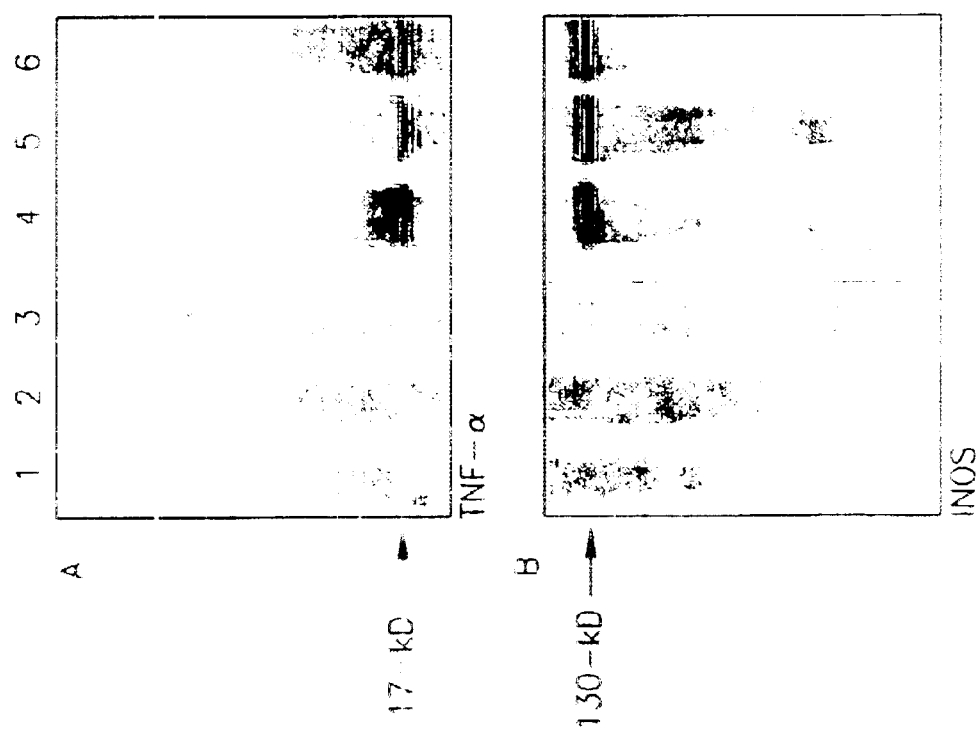

Increased production of TNF-α and NO by glial cells in response to stressors: The possibility that production of TNF-α and NOS by glial cells was examined in co-cultures exposed to stress conditions was directly involved in facilitating retinal ganglion cell apoptosis. Western blot analysis using cell lysates revealed that the expression of TNF-α and iNOS was undetectable in retinal ganglion cells incubated under either normal or stress conditions. However, the expression of TNF-α and iNOS increased in glial cells in co-cultures exposed to simulated ischemia or elevated hydrostatic pressure (FIGS. 11a and b). Immunocytochemistry similarly demonstrated increased expression of TNF-α and iNOS in glial cells in co-cultures incubated under stress conditions (FIGS. 11c–h).

Figure 12A:
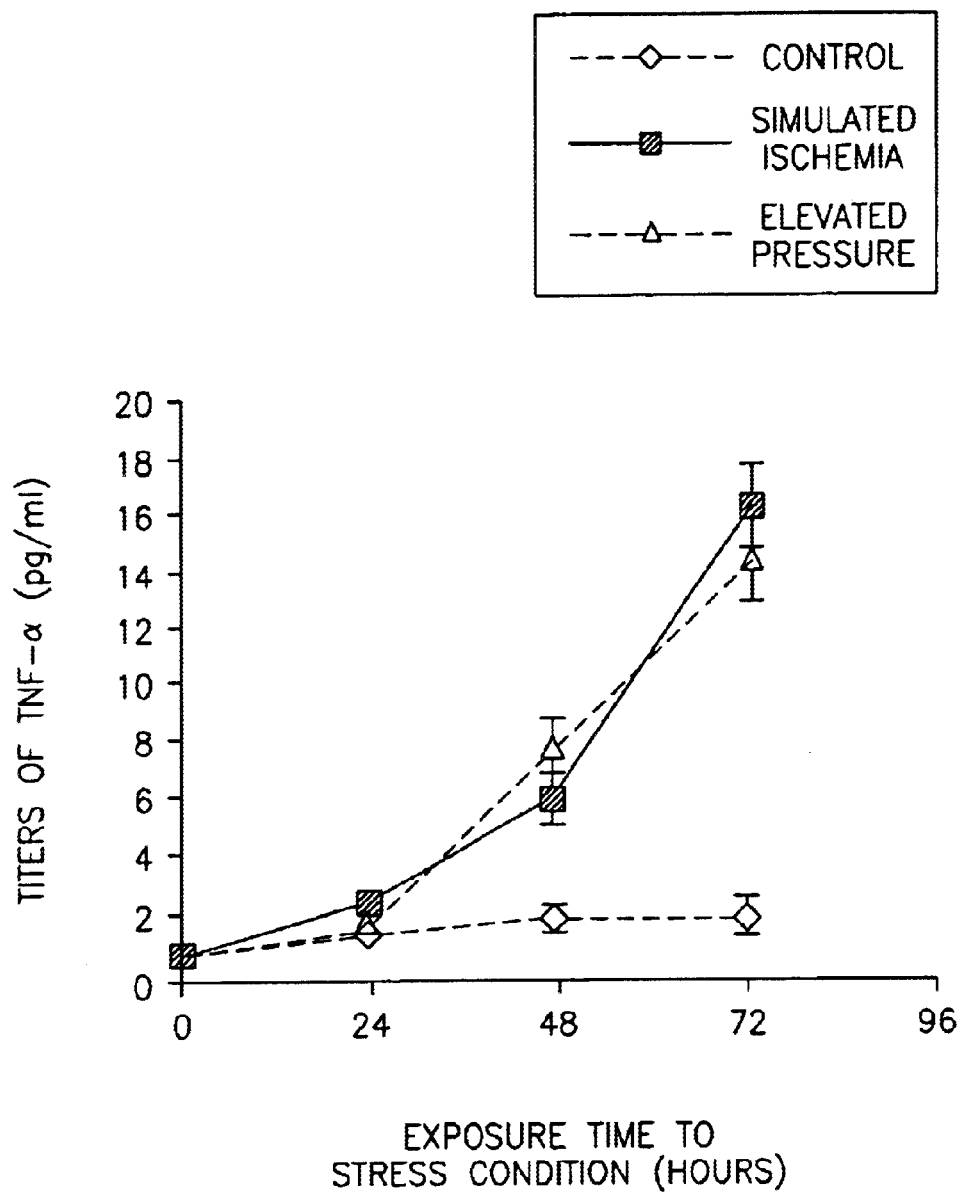
FIG. 12. Measurement of TNF-α and end products of NO in conditioned medium of co-cultures incubated under stress conditions. (a) Titers of TNF-α in conditioned medium as measured by ELISA. (b) Titers of end products of NO in conditioned medium as measured by a colorimetric assay.
Figure 12B:
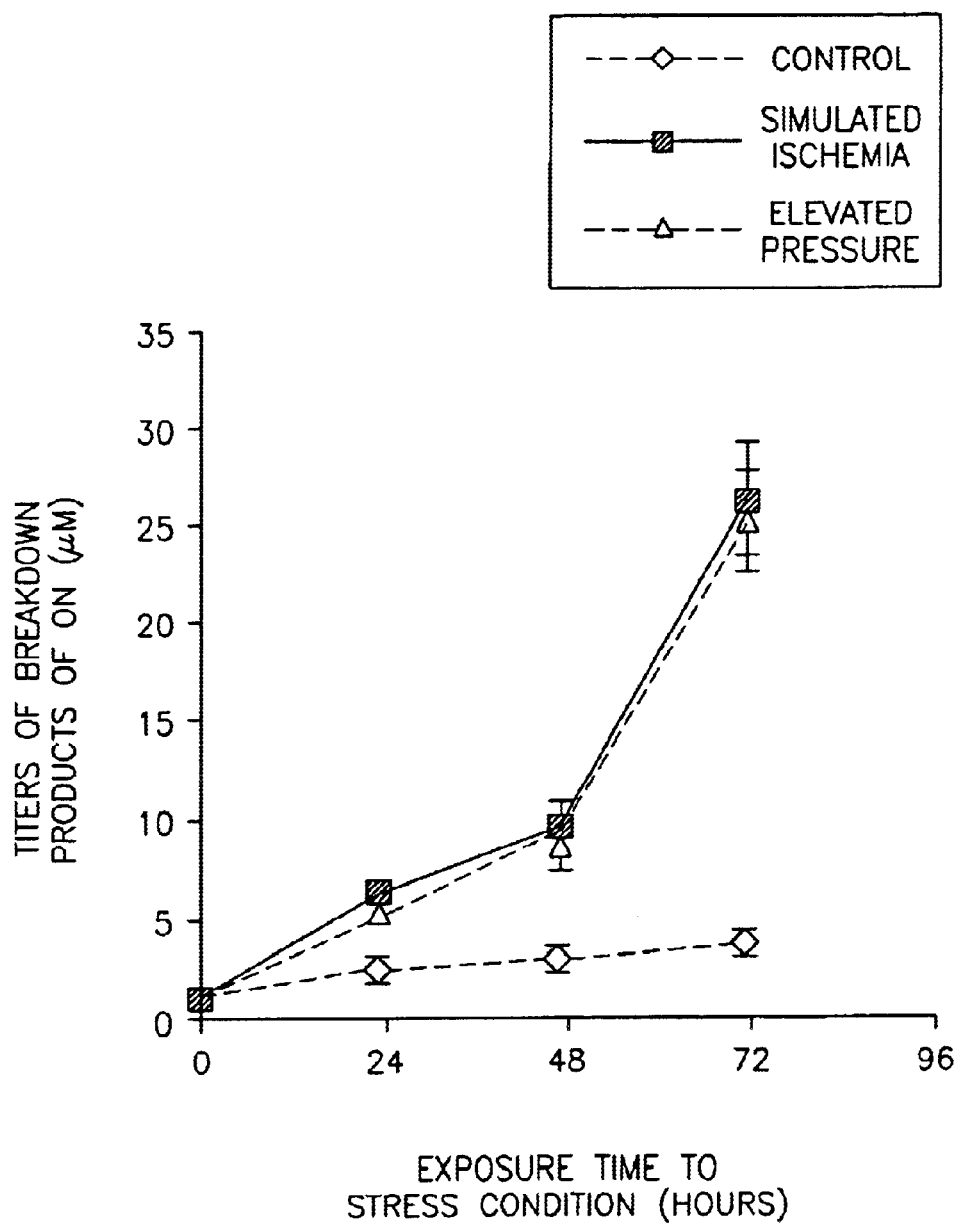

The levels of TNF-α and end products of NO in conditioned medium of the co-cultures was measured. TNF-α levels in the conditioned medium measured by ELISA were approximately 8 times higher in co-cultures exposed to simulated ischemia or elevated hydrostatic pressure compared to co-cultures incubated under normal condition (Mann-Whitney U test, p=0.003) (FIG. 6a). As measured by a colorimetric assay, breakdown products of NO in conditioned medium increased approximately 7 fold in co-cultures exposed to stress conditions compared to co-cultures incubated under normal condition (p=0.003) (FIG. 12b).

Figure 13:
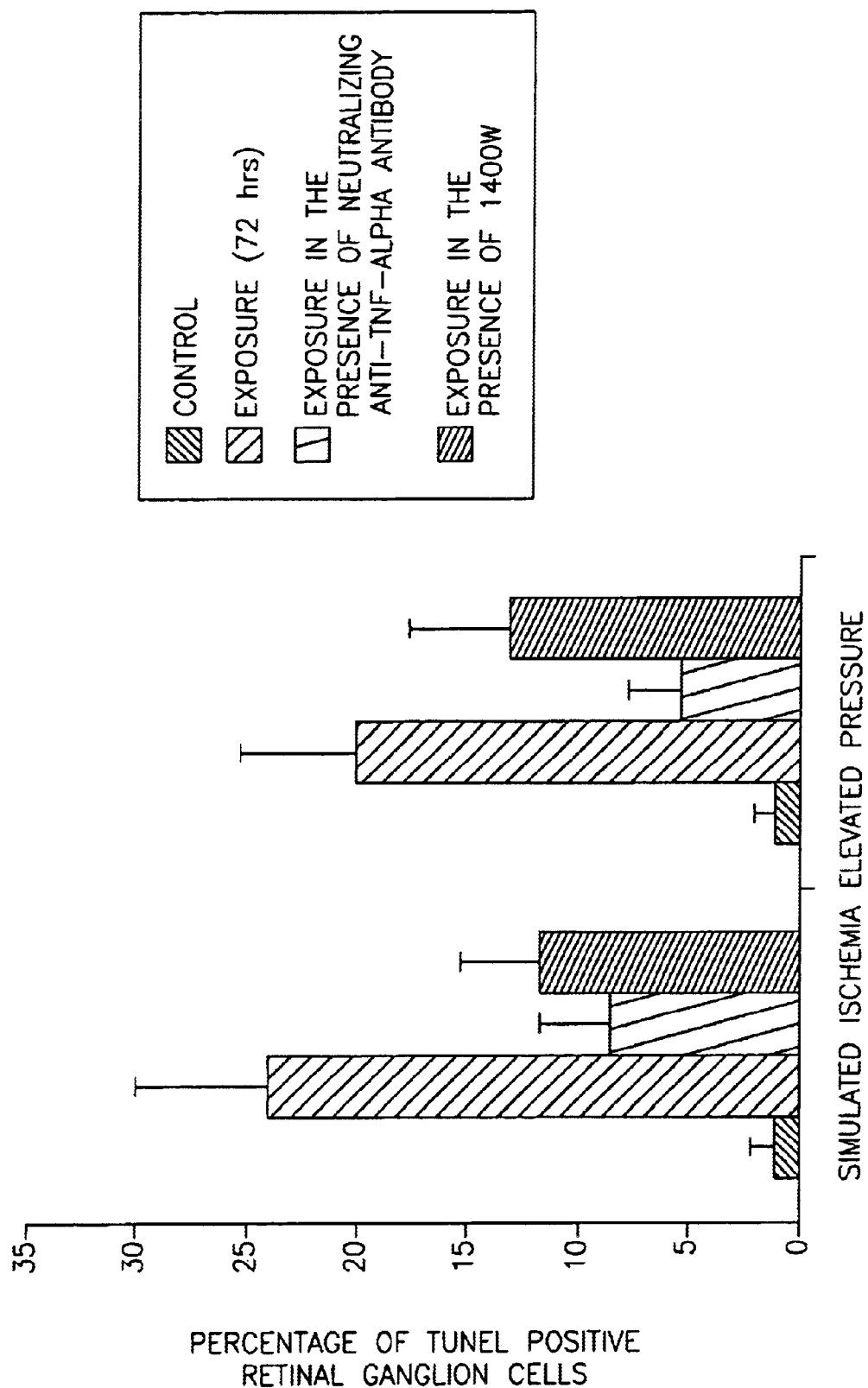
FIG. 13. Inhibition of apoptosis in retinal ganglion cells in co-cultures incubated under stress conditions in the presence of specific inhibitors of TNF-α or iNOS. The activity of TNF-α was neutralized using a specific antibody (10 μg/ml) and iNOS was inhibited using a selective inhibitor, 1400W (2.5 μM).

In addition, experiments were performed in which co-cultures were incubated under stress conditions in the presence of specific inhibitors of TNF-α or iNOS. The experiments revealed that inhibitors of TNF-α or iNOS were able to diminish apoptotic cell death in retinal ganglion cells induced by simulated ischemia or elevated hydrostatic pressure. Inhibition of the bioactivity of TNF-α by a specific neutralizing antibody (AF510NA, 10 ug/ml) resulted in decreased rate of positive TUNEL from 24% to 8% (67%) in co-cultures incubated under simulated ischemia and from 20% to 5% (75%) in co-cultures incubated under elevated hydrostatic pressure (Mann-Whitney U test, p=0.0002). Treatment of co-cultures with 2.5 uM of the selective inhibitor of iNOS, 1400W, decreased the rate of positive TUNEL approximately 50% in co-cultures incubated under simulated ischemia and approximately 35% in co-cultures incubated under elevated hydrostatic pressure (p=0.003) (FIG. 13). Inhibition of apoptosis by neutralizing antibody against TNF-α was more prominent than at by 1400W (p=0.008).

REFERENCES

1. Hewett, S. J., Csernansky, C. A. & Choi, D. W. Selective potentiation of NMDA-induced neuronal injury following induction of astrocytic iNOS. *Neuron* 13, 487–494 (1994).
2. Dugan, L. L., Bruno, V. M. G., Amagasu, S. M. & Giffard, R. G. Glia modulate the response of murine cortical neurons to excitotoxicity; glia exacerbate AMPA neurotoxicity. *J. Neurosci.* 15, 4545–4555 (1995).
3. Ridet, J. L., Malhotra, S. K., Privat, A. & Gage, F. H. Reactive astrocytes: cellular and molecular cues to biological function. *Trends Neurosci.* 20, 570–577 (1997).
4. Viviani, B., Corsini, E., Galli, C. L. & Marinovich, M. Glia increase degeneration of hippocampal neurons through release of tumor necrosis factor-□. *Toxicol. App. Pharmacol.* 150, 271–276(1998).
5. Vandenberghe, W., Bosch, L. V. D. & Robberecht, W. Glial cells potentiate kainate-induced neuronal death in a motoneuron-enriched spinal coculture system. *Brain Res.* 807, 1–10 (1998).
9. Raivich, G. et al. Neuroglial activation in the injured brain; graded response, molecular mechanisms and cues to physiological function. *Brain Res. Review* 30, 77–105 (1999).

7. Hernandez, M. R. & Pena, J. D. The optic nerve head in glaucomatous optic neuropathy. *Arch. Ophthalmol.* 115, 389–395 (1997).
8. Quigley, H. A. et al. Retinal ganglion cell death in experimental glaucoma and after axotomy occurs by apoptosis. *Invest. Ophthalmol. Vis. Sci.* 36, 774–786 (1995).
9. Neufeld, A. H., Hernandez, M. R. & Gonzalez, M. Nitric oxide synthase in the human glaucomatous optic nerve head. *Arch. Ophthalmol.* 115, 497–503 (1997).
10. Yan, X., Tezel, G., Edward, D. P. & Wax, M. B. Matrix metalloproteinases and tumor necrosis factor-□ in glaucomatous optic nerve head. *Arch. Ophthalmol.* (2000) In press.
11. de Kozak. Y., Cotinet, A., Goureau, O., Hicks, D. & Thillaye-Goldenberg, B. Tumor necrosis factor and nitric oxide production by resident retinal glial cells from rats presenting hereditary retinal degeneration. *Ocul. Immunol. Inflamm.* 5, 85–94 (1997).
12. Cotinet A., Goureau, O., Hicks, D., Thillaye-Goldenberg, B. & de Kozak, Y. Tumor necrosis factor and nitric oxide production by retinal Muller glial cells from rats exhibiting inherited retinal dystrophy. *Glia* 20, 59–69 (1997).
13. Goureau, O., Regnier-Ricard, F. & Courtois, Y. Requirement for nitric oxide in retinal neuronal cell death induced by activated Muller glial cells. *J. Neurochem.* 72, 2506–2515 (1999).
14. Hitchings, R. A. & Spaeth, G. L. Fluorescein angiography in chronic simple and low-tension glaucoma. *Br. J. Ophthalmol.* 61, 126–132 (1977).
15. Drance, S. M., Shulzer, M., Douglas, G. R. & Sweeney, V. P. Use of discriminant analysis. Identification of persons with glaucomatous visual field defects. *Arch. Ophthalmol.* 96, 57–73 (1978).
16. Hart. W. M. N., Yablonski, M., Kass, M. A. & Becker, B. Multivariate analysis of the risk of glaucomatous visual field loss. *Arch. Ophthalmol.* 97, 1455–1458 (1979).
17. Barres, B. A., Silverstein, B. E., Corey, D. P. & Chun, L. L. Y. Immunological, morphological and electrophysiological variation among retinal ganglion cells purified by panning. *Neuron* 1, 791–803 (1998).
18. Kitano, S., Morgan, J. & Caprioli, J. Hypoxic and excitotoxic damage to cultured rat retinal ganglion cells. *Exp. Eye Res.* 63, 105–112 (1996).
19. Hayreh, S. S. Inter-individual variation in blood supply of the optic nerve head. Its importance in various ischemic disorders of the optic nerve head, and glaucoma, low-tension glaucoma and allied disorders. *Doc. Ophthalmol.* 59, 217–46 (1985).
20. Anderson, D. R. & Hendrickson, A. Effect of intraocular pressure on rapid axoplasmic transport in monkey optic nerve. *Invest. Ophthalmol. Vis. Sci.* 13, 771–7183 (1974).
21. Minckler, D. S., Tso, M. O. & Zimmerman L. E. A light microscopic, autoradiographic study of axoplasmic transport in the optic nerve head during ocular hypotony, increased intraocular pressure, and papilledema. *Am. J. Ophthalmol.* 82, 741–757 (1976).
22. Quigley, H. A. & Addicks, E. M. Chronic experimental glaucoma in primates. II. Effect of extended intraocular pressure elevation on optic nerve head and axonal transport. *Invest. Ophthalmol. Vis. Sci.* 19, 137–152 (1980).
23. Pease, M. E., McKinnon, S. J., Quigley, H. A., Kerrigan-Baumrind, L. A. & Zack, D. J. Obstructed axonal transport of BDNF and its receptor TrkB in experimental glaucoma. *Invest. Ophthalmol. Vis. Sci.* 41, 764–774 (2000).
24. Flammer, J. The vascular concept of glaucoma. *Surv. Ophthalmol.* 38 (Suppl), S3–S6 (1994).
25. Yamamoto, T. & Kitazawa, Y. Vascular pathogenesis of normal-tension glaucoma: a possible pathogenetic factor, other than intraocular pressure, of glaucomatous optic neuropathy. *Prog. Retin. Eye Res.* 17, 127–43 (1998).
26. Chung, H. S. et al. Vascular aspects in the pathophysiology of glaucomatous optic neuropathy. *Surv. Ophthalmol.* 43, Suppl 1:S43–50 (1999).
27. Takano, K. J., Takano, T., Yamanouchi, Y. & Satau, T. Pressure-induced apoptosis in human lymphoblasts. *Exp. Cell Res.* 235, 155–160 (1997).
28. Takahashi, K. et al. Hydrostatic pressure induces expression of interleukin 6 and tumor necrosis factor □ mRNA in a chondrocyte-like cell line. *Ann. Rheum. Dis.* 57, 231–236 (1998).
29. Wax, M. B., Tezel, G., Kobayashi, S. & Hernandez, M. R. Responses of different cell lines from ocular tissues to elevated hydrostatic pressure. *Br. J. Ophthalmol* 84, 423–428 (2000).
30. Liu, T. et al. Tumor necrosis factor-α expression in ischemic neurons. *Stroke* 25, 1481–1488 (1994).
31. Barone, F. C. et al. Tumor necrosis factor-□. A mediator of focal ischemic brain injury. *Stroke* 28, 1233–1244 (1997).
32. Semenzato, G. Tumor necrosis factor: a cytokin with multiple biological activity. *Br. J. Cancer* 61, 354–361 (1990).
33. Brenner, T., Yamin, A., Abramsky, O. & Gallily, R. Stimulation of tumor necrosis factor-alpha production by mycoplasma and inhibition by dexamethasone in cultured astrocytes. *Brain Res.* 608, 273–279 (1993).
34. Lieberman, A. P., Pitha, P. M., Shin, H. S. & Shin, M. L. Production of tumor necrosis factor and other cytokines by astrocytes stimulated with lipopolysaccharide or a neurotropic virus. *Proc. Natl. Acad. Sci. USA* 86, 6348–6352 (1989).
35. Meda, L. et al. Activation of microglial cells by □-amyloid protein and interferon-□. *Nature* 374, 647–650 (1995).
36. de Vos. A. F., Klaren, V. N. & Kijlstra, A. Expression of multiple cytokines and IL-1RA in the uvea and retina during endotoxin-induced uveitis in the rat. *Invest. Ophthalmol. Vis. Sci.* 35, 3873–3883 (19941).
37. Planck, S. R., Huang, X. N., Robertson, J. E. & Rosenbaum, J. T. Cytokine mRNA levels in rat ocular tissues after systemic endotoxin treatment. *Invest. Ophthalmol. Vis. Sci.* 35. 924–930 (1994).
38. Drescher, K. M. & Whittum-Hudson, J. A. Modulation of immune-associated surface markers and cyokine production by murine retinal glial cells. *J. Neuroimmunol.* 64, 71–81 (1996).
39. McGeer, P. L. et al. Microglia in degenerative neurological disease. *Glia* 7, 84–92 (1993).
40. Rothwell, N. J. & Hopkins, S. J. Cytokines and the nervous system II: actions and mechanisms of action. *Trends Neurosci.* 18, 130–136 (1995).
41. Martin-Villalba, A. et al. CD95 ligand (Fas-L/APO-1L) and tumor necrosis factor-related apoptosis-inducing ligand mediate ischemia-induced apoptosis in neurons. *J. Neurosci.* 19, 3809–3817 (1999).
42. Ertel, W. et al. Release of anti-inflammatory mediators after mechanical trauma correlates with severity of injury and clinical outcome. *J. Trauma* 39, 879–885 (1995).
43. Shohami, E., Bass, R.,. Wallach, D., Yamin, A. & Gallily, R. Inhibition of tumor necrosis alpha (TNF□□) activity in rat brain is associated with cerebroprotection after 44. Lin, X. et al. An immunohistochemical study of TNF-□ in optic nerves from AIDS patients. *Curr. Eye Res.* 16, 1064–1068 (1997).
45. Madigan, M. C. et al. Tumor necrosis factor -alpha (TNF-□□□induced optic neuropathy in rabbits. *Neurol. Res.* 18, 176–184 (1996).
46. Hsu, H., Xiong, J. & Goeddel, D. V. The TNF receptor 1-associated protein TRADD signals cell death and NF-kappa B activation. *Cell* 81, 495–504 (1995).
47. Dawson, V. L., Brahmbhatt, H. P., Mong, J. A. & Dawson, T. M. Expression of inducible nitric oxide synthase causes delayed neurotoxicity in primary mixed neuronal-glial cortical cultures. *Neuropharmocology* 33, 1425–1430 (1994).
48. Bredt, D. S. & Snyder, S. H. Nitric oxide: a physiologic messenger molecule. *Annu Rev. Biochem.* 63, 175–195 (1994).
49. Iadecola, C., Zhang, F. & Xu, X. Inhibition of inducible nitric oxide synthase ameliorates cerebral ischemic damage. *Am. J. Physiol.* 268, R296–R292 (1995).
50. Liu, J., Zhao, M.-L., Brosnan C. F. & Lee, S. C. Expression of type II nitric oxide synthase in primary human astrocytes and microglia: role of IL-1□ and IL-1 receptor antagonist. *J. Immunol.* 157, 3569–3576 (1996).
51. Park. C. S., Pardhasaradhi, K., Gianotti, C., Villegas, E. & Krishna, G. Human retina expresses both constitutive and inducible isoforms of nitric oxide synthase mRNA. *Biochem Biophys. Res. Commun.* 205, 85–91 (1994).
52. Perez, M. T., Larsson, B., Alm, P., Anderson, K. E. & Ehinger, B. Localization of neuronal nitric oxide synthase-immunoreactivity in rat and rabbit retinas. *Exp. Brain Res.* 104, 207–217 (1995).
53. Shin, D. H. et al. In situ localization of neuronal nitric oxide synthase (nNOS) mRNA in the rat retina. *Neurosci. Lett.* 270, 53–55 (1999).
54. Kim, J. B. et al. Immunocytochemical localization of nitric oxide synthase in the mammalian retina. *Neurosci. Lett.* 267, 193–196 (1999).
55. Goureau, O., Hicks, D., Courtois, Y. & De Kozak, Y. Induction and regulation of nitric oxidesynthase in retinal Muller glial cells. *J. Neurochem.* 63, 310–317 (1994).
56. Roth, S. Role of nitric oxide in retinal cell death. *Clin. Neurosci.* 4, 216–223 (1997).
57. Koeberle, P. D. & Ball, A. K. Nitric oxide synthase inhibition delays axonal degeneration and promotes the survival of axotomized retinal ganglion cells. *Exp. Neurol.* 158, 366–381 (1999).
58. Kashii, S. et al. Dual actions of nitric oxide in N-methyl-D-aspartate-mediated neurotoxicity in cultured retinal neurons. *Brain Res.* 711, 93–101 (1996).
59. Morgan, J., Caprioli, J. & Koseki, Y. Nitric oxide mediates excitotoxic and anoxic damage in rat retinal ganglion cells cocultured with astroglia. *Arch. Ophthalmol.* 117, 1524–1529 (1999).
60. Lam, T. & Tso, M. Nitric oxide synthase (NOS) inhibitors ameliorate retinal damage induced by ischemia in rats. *Res. Commun. Mol. Pathol. Pharmol.* 92, 329–340 (1996).
61. Shareef, S., Sawada, A. & Neufeld, A. H. Isoforms of nitric oxide synthase in the optic nerves of rat eyes with chronic moderately elevated intraocular pressure. *Invest. Ophthalmol. Vis. Sci.* 40, 2884–2891 (1999).
62. Neufeld, A. H., Sawada, S. & Becker, B. Inhibition of nitric oxide synthase-2 by aminoguanidine provides neuroprotection of retinal ganglion cells in a rat model of glaucoma. *Proc. Natl. Acad Sci. USA* 96, 9944–9948 (1999).
63. Shafer, R. A. & Murphy, S. Activated astrocytes induce nitric oxide synthase-2 in cerebral endothelium via tumor necrosis factor alpha. *Glia* 21, 370–379 (1997).
64. Goureau, O., Amiot, F., Dautry, F. & Courtois. Y. Control of nitric oxide production by endogenous TNF-alpha in mouse retinal pigmented epithelial and Muller glial cells. *Biochem. Biophys. Res. Commun.* 240, 132–135 (1997).
65. Heneka, M. T. et al. Induction of nitric oxide synthase and nitric oxide-mediated apoptosis in neuronal PC12 cells after stimulation with tumor necrosis factor-alpha/lipopolysaccharide. *J. Neurochem.* 71, 88–94 (1998).
66. Perkins, D. J. et al. Reduction of NOS2 overexpression in rheumatoid arthritis patients with anti-tumor necrosis factor a monoclonal antibody (cA2). *Arthritis Rheum.* 41, 2205–2210 (1998).
67. Sartani, G. et al. Anti-tumor necrosis factor alpha therapy suppresses the induction of experimental autoimmune uveoretinitis in mice by inhibiting antigen priming. *Invest. Ophthalmol. Vis. Sci.* 37, 2211–2218 (1996).
68. Dick, A. D. et al. Inhibition of tumor necrosis factor activity minimizes target organ damage in experimental autoimmune uveoretinitis despite quantitatively normal activated T cell traffic to the retina. *Eur. J. Immunol.* 26, 1018–1025 (1996).
69. Wray, G. M., Millar, C. G., Hinds, C. J. & Thiemermann, C. Selective inhibition of the activity of inducible nitric oxide synthase prevents the circulatory failure, but not the organ injury/dysfunction caused by endotoxin. *Shock* 9, 329–335 (1998).
70. Tezel, G., Seigel, G. M. & Wax, M. B. Density-dependent resistance to apoptosis in retinal cells. *Curr. Eye Res.* 19, 377–388 (1999).
71. Metzger, D. W., Metzger, C. A., Ling, L. A., Hurst, J. S. & van Cleave, V. H. Preparative isolation of murine CD5 B cells by panning and magnetic beads. *Ann. NY Acad. Sci.* 651. 75–77 (1992).
72. Wright, A. P., Fitzgerald, J. J. & Colello, R. J. Rapid purification of glial cells using immunomagnetic separation. *J. Neurosci. Methods* 74, 37–44 (1997).
73. Aotaki-Keen, A. E., Harvey, A. K., de Juan, E. & Hjelmeland, L. M. Primary culture of human retinal glia. *Invest. Ophthalmol. Vis. Sci.* 32, 1733–1738 (1991).
74. Brewer, G. J., Torricelli, J. R., Evege, E. K. & Price, P. J. Optimized survival of hippocampal neurons in B27-supplemented Neurobasal™, a new serum-free medium combination. *J. Neurosci. Res.* 35, 567–576 (1993).
75. Jo, S. A., Wang, E. & Benowitz, L. I. Ciliary neurotrophic factor is an axogenesis factor for retinal ganglion cells. *Neuroscience* 89, 579–591 (1999).
76. Selles-Navarro, I., Villegas-Perez, M. P., Salvador-Silva, M., Ruiz-Gomez, J. M. & Vidal-Sanz, M. Retinal ganglion cell death after different transient periods of pressure-induced ischemia and survival intervals. *Invest. Ophthalmol. Vis. Sci.* 37, 2002–2014. (1996).
77. Barone. F. C. et al. Tumor Necrosis Factor-□□ A Mediator of Focal Ischemic Brain Injury. *Stroke* 28, 1233–1244 (1997).
78. Lavine, S. D., Hoffman, F. M. & Zlokovic, B. V. Circulating antibody against tumor necrosis factor-alpha protects rat brain from reperfusion injury. *J. Cereb. Blood Flow Metab.* 18, 52–58 (1999).
79. Downen, M., Amaral, T. D., Hua, L. L., Zhao, M.-L. & Lee, S. C. Neuronal death in cytokine-activated primary human brain cell culture: role of tumor necrosis factor-□. *Glia* 28, 114–127 (1999).
80. Garvey, E. P. et al. 1400W is a slow tight binding and highly selective inhibitor of inducible nitric-oxide synthase in Vitro and in Vivo. *J. Biol Chem.* 272, 4959–4963 (1997).

81. Haugland, R. P. & Larison, K. D. *Handbook of fluorescent probes and research chemicals*. 5th ed. Eugene, Oreg.: Molecular Probes, 172–180 (1994).
82. Gavrieli, Y., Sherman, Y. & Ben-Sasson, S. A. Identification of programmed cell death in situ via specific labeling of nuclear DNA fragmentation. *J. Cell Biol.* 119, 493–501 (1992).
83. Finucane, D. M., Bossy-Wetzel, E., Waterhouse, N. J., Cotter, T. G. & Green, D. R. Bax-induced caspase activation and apoptosis via cytochrome c release from mitochondria is inhibitable by Bcl-xL. *J. Biol. Chem.* 274, 2225–2233 (1999).

What is claimed is:

1. A method for treating a subject with glaucoma comprising the steps of administrating a compound or composition containing an agent, which antagonize, inhibits, inactivates, reduce, suppresses, antagonizes, and/or limits the release, synthesis, or production from cells of TNF-α thereby treating the subject with glaucoma.

2. The method of claim 1, wherein the compound or composition suppresses the level or production of TNF-α.

3. The method of claim 1, wherein the compound or composition inactivates circulating TNF-α.

4. The method of claim 1, wherein the molecule is anti-TNF-α antibody.

5. The method of claim 4, wherein the molecule is a monoclonal or polyclonal antibody.

6. The method of claim 5, wherein the molecule is infliximab.

7. A pharmaceutical composition of claim 1 and a diluent and suitable carrier.

8. The method of claim 1, wherein the compound or composition is administered ocularly, parenterally, transmucosally, transdermally, intramuscularly, intravenously, intradermally, intravascularly, or subcutaneously, intraperitonealytopical drops or ointment, periocular injection, systemically by intravenous injection or orally, intracamerally into the anterior chamber or vitreous, via a depot attached to the intraocular lens implant inserted during surgery, or via a depot placed in the eye sutured in the anterior chamber or vitreous.

* * * * *